(12) United States Patent
Southern

(10) Patent No.: US 8,771,962 B2
(45) Date of Patent: *Jul. 8, 2014

(54) HEALTH TEST FOR A BROAD SPECTRUM OF HEALTH PROBLEMS

(76) Inventor: Sarka O. Southern, San Diego, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 13/122,130

(22) PCT Filed: Oct. 2, 2009

(86) PCT No.: PCT/US2009/059438
§ 371 (c)(1),
(2), (4) Date: Jun. 17, 2011

(87) PCT Pub. No.: WO2010/040097
PCT Pub. Date: Apr. 8, 2010

(65) Prior Publication Data
US 2011/0251096 A1   Oct. 13, 2011

Related U.S. Application Data

(60) Provisional application No. 61/102,341, filed on Oct. 2, 2008.

(51) Int. Cl.
*G01N 33/53* (2006.01)
(52) U.S. Cl.
USPC ............................................. 435/7.1; 435/7.2
(58) Field of Classification Search
None
See application file for complete search history.

(56) References Cited

U.S. PATENT DOCUMENTS

| | | | |
|---|---|---|---|
| 2002/0090620 A1* | 7/2002 | Davis et al. | 435/6 |
| 2003/0073160 A1 | 4/2003 | Boux | |
| 2003/0082597 A1 | 5/2003 | Cannon et al. | |
| 2004/0029208 A1* | 2/2004 | Ravn | 435/29 |
| 2008/0038760 A1* | 2/2008 | Mascart et al. | 435/7.92 |

FOREIGN PATENT DOCUMENTS

| | | |
|---|---|---|
| WO | WO 01/92879 A1 | 12/2001 |
| WO | WO 2005/034727 A2 | 4/2005 |
| WO | WO 2005/050224 A2 | 6/2005 |
| WO | WO 2007/045865 A2 | 4/2007 |

OTHER PUBLICATIONS

Chiappelli et al. (Bioinformation 2006 vol. 1, p. 331-334).*
Takai et al. (Archives of oral biology 2004 vol. 49, p. 963-968).*
Chiappelli et al., "Salivary Biomarkers in Psychobiological Medicine," *Bioinformation* (2006), 1(8):331-334, Biomedical Informatics Publishing Group.
Southern and Lilienthal, "New technology for early detection of health threats", *Proc. of SPIE*, vol. 6945, pp. 6945F-1-6945F-7 (2008).
Chiappelli et al: "Salivary biomarkers in psychobiological medicine", Bioinformation, vol. 1, No. 8, Dec. 29, 2006, pp. 331-334, XP008136863,ISSN: 0973-2063.
Streckfus C F et al: "Saliva as a diagnostic fluid", Oral Diseases, Stockton Press, Basingstoke, GB, vol. 8, No. 2, Mar. 21, 2002, pp. 69-76, XP002518738,ISSN: 135-523X, DOI: 10.1034/J.1601-0825. 2002.10834.X.

* cited by examiner

*Primary Examiner* — Jacob Cheu
(74) *Attorney, Agent, or Firm* — DLA Piper LLP (US)

(57) ABSTRACT

Provided herein are methods and devices for the detection of conditions or disorders by detecting altered levels of stress response pathway biomarkers. Also provided are methods and reagents for identifying panels of biomarkers associated with a condition or disorder.

17 Claims, 7 Drawing Sheets

HEALTH TEST FOR A BROAD SPECTRUM OF HEALTH PROBLEMS

CROSS REFERENCE TO RELATED APPLICATIONS

This application is a 35 USC §371 National Stage application of International Application No. PCT/US2009/050438 filed Oct. 2, 2009, now pending; which claims the benefit under 35 USC §119(e) to U.S. Application Ser. No. 61/102,341 filed Oct. 2, 2008, now expired. The disclosure of each of the prior applications is considered part of and is incorporated by reference in the disclosure of this application.

FIELD OF THE INVENTION

The present invention relates generally to a device for detecting a stress response in a sample, and more specifically to methods of detecting a stress biomarker in a sample.

BACKGROUND INFORMATION

Wellness products and services are increasingly popular, particularly in developed countries. Many are rooted in the traditional medicine, e.g. body care products, natural medicines, massage, acupuncture, sauna, spa treatments. New products and services include handheld devices for vital sign measurements, tests for 'good' or 'bad' metabolites such as antioxidants or cholesterol, and treatments such as cold laser or hyperbaric oxygen. Wellness products and services are sold at retail stores, walk-in clinics, integrative medicine facilities, health spas and gyms and through electronic healthcare companies that also provide integrated wellness services. Wellness products and services are typically selected using generalized recommendations (e.g. age and gender based), subjective tests such as health questionnaires and the pain scale, vital signs (blood pressure), weight and metabolite tests (e.g. cholesterol or glucose). New test are needed for personalized assessment of health, identification of the need for wellness products and selecting the best match for the personal need. Optimally, new tests will provide an early warning of a health problem and indicate the nature of the problem. In addition, new tests showing specific health benefits of wellness products and services are needed, in addition to the available anti-oxidant tests for nutritional supplements.

There is an urgent need for a new health test suitable for point-of-care (POC) settings. The test should be noninvasive and capable of detecting early signs of deteriorating health status. To be POC-expedient, the test should be rapid, technically simple and inexpensive.

SUMMARY OF THE INVENTION

In accordance with the present invention, there are provided POC devices useful for Stress Response Profiling (SRP) in saliva. In one embodiment, the device is a hand-held digital device for mobile health monitoring (FIG. 6). The use of the device is intuitive (similar to a digital thermometer) and does not require training for use. The test is noninvasive, rapid and inexpensive, and capable of detecting early warnings of health problems. The SRP device can be used for preventative POC health screening, consumer-centric wellness care, routine clinical care, it can be used in emergency rooms and trauma units, it can be used by first responders, by individuals for chronic disease management, it can be used in complementary and alternative medicine, military healthcare.

In accordance with the present invention, there are provided devices for detecting at least one stress response biomarker in a test sample. Such devices include a disposable module for uptake of a test sample and reagent storage, wherein the module contains reagents for assaying for at least one stress response biomarker; and a reusable module for signal detection and result display; wherein the reusable module displays a signal that indicates the presence of the at least one stress response biomarker in the test sample. In some embodiments, the signal provides a digital readout of a percentage above a baseline representing the presence of the at least one stress response biomarker in the test sample. In certain embodiments, the signal provides a visual indication representing the presence of the at least one stress response biomarker in the test sample. In one aspect, the visual indication is a color indication.

The device may be used to test a biological sample. In some embodiments, the test sample is selected from the group containing breath air, saliva, urine, sweat, tears, blood, serum, stool, phlegm, bone marrow, cerebrospinal fluid, seminal fluid, vaginal fluid, amniotic fluid, skin, breast milk, tissue, plant sap, an egg, microbial body, cells suspension or a combination thereof.

In certain embodiments, the device further includes a means for accessing a database, wherein the database provides a correlation between the presence of the at least one stress biomarker molecule in the test sample and (i) the presence, absence, or severity, if present, of a particular disease state; or (ii) the likelihood that an organism from which the test sample was obtained will contract or be subject to a particular disease state.

In some embodiments, the device assays for at least one stress response biomarker selected from the group consisting of aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide. In one aspect, the device includes at least one stress biomarker associated with dehydration. In another aspect, the device includes at least one stress biomarker associated with AIDS progression.

In another embodiment of the invention, there are provided methods for detecting a condition or disorder associated with a stress response in a subject. The methods include detecting an altered level of at least one biomarkers in an stress response biomarker panel in a sample comprising salivary cells from a subject, as compared to a corresponding sample from a normal subject, wherein the panel comprises at least two biomarkers, and wherein further an alteration in the level of biomarker is indicative of a stress response associated with the condition or disorder, thereby detecting the condition or disorder in the subject. In particular embodiments, the at least one stress response biomarker is selected from the group consisting of aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide. In one aspect, the method includes at least one stress biomarker associated with dehydration. In another aspect, the method includes at least one stress biomarker associated with AIDS progression.

In some embodiments, the levels of the at least one biomarker are detected by analysis of biomarker protein or nucleic acid in the sample comprising the salivary cells. In particular embodiments, the analysis of biomarker protein includes detection with an antibody. In one aspect, the salivary cells are lysed prior to analysis with the antibody. The analysis may be conducted by ELISA or other antibody detection methods known in the art. In certain embodiments, the levels of the at least one biomarker are assayed using a device of the invention. In some embodiments, the sample containing the salivary cells is analyzed on microscope slide.

In other embodiments, the analysis of biomarker nucleic acid comprises isolation of salivary cell nucleic acid. In one aspect, the biomarker nucleic acid is detected in the isolated salivary cell nucleic acid by nucleic acid hybridization or PCR amplification.

In another embodiment of the invention there are provided methods of processing a salivary cell sample for biomarker analysis. Such methods include applying a sample of saliva or salivary cells to a substrate; fixing the cells; incubating the cells in low pH citrate buffer at 37° C.; contacting the cells with serum; applying a primary antibody for each of biomarker of a biomarker panel; and detecting the binding of the primary antibody using a secondary antibody having a detectable label, wherein the label is detected optically using a computerized image analysis. In certain embodiments, the salivary cells are collected using an oral brush. In some embodiments, the biomarker panel comprises at least one biomarker selected from the group consisting of aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide.

In another embodiment of the invention, there are provided methods for constructing a biomarker panel for detecting a stress response in a cultured cell. The method includes detecting the level of one or more biomarkers from a panel of biomarkers in cultured cells subjected to a treatment that induces cellular stress; and comparing the level of the biomarkers from the treated cells to the level of the biomarker from a corresponding sample of cultured cells that have not been subjected to the treatment that induces cellular stress, wherein biomarkers having a difference level in the treated cells as compared to the untreated cells are included in an SR biomarker panel for a stress response. In particular embodiments, the treatment that induces cellular stress is a stressor selected from the group consisting of heat shock, freeze/thaw cycling, hypersalinity, dehydration, and oxidative stress. In some embodiments, the cultured cells are salivary cells, peripheral blood mononuclear cells, or cells from organ cultures of tonsil, skin, gut or lung. In particular embodiments, the cells are animal cells. In one aspect, the cells are human cells.

DETAILED DESCRIPTION OF THE INVENTION

1. SRP Technology

Figure 1:
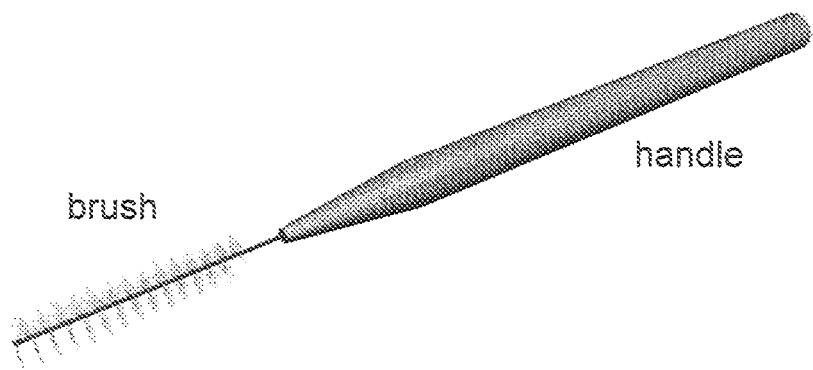
FIG. 1 shows an illustration of device for collecting saliva samples.

Stress Response Profiling (SRP) is a recently developed technology that uses molecular biomarkers for multiparametric measurements of physiological stress responses. The SRP measurement serves as a novel vital sign. SRP is applicable to a broad spectrum of health threats including environmental stressors, metabolic stressors, psychological trauma, injuries and diseases. SRP measurements quantify physiological stress and also discriminate between different types of health disorders. SRP biomarkers monitor ten principal homeostatic processes (Table 1).

As used herein, the term "homeostasis" is a biological process that maintains the health of organisms.

As used herein, the term "persistent homeostatic perturbation" is to be understood as a homeostatic change that has an adverse affect on the health of organisms. It is another way of referring to "chronic stress" or simply "stressed" which should be understood to mean a persistent perturbation of homeostasis and encompassing all forms of chronic cellular stress and chronic physiological stress.

As used herein, the term "stressor" is to be understood as all forms of agents or conditions that give rise to stress. Stressors according to the present invention include agents and conditions that are in the outer environment of organisms such as the air temperature as well as agents and conditions that are in the inner environment of organisms such as a disease.

As used herein, the term "adaptive stress response" or simply "stress response" is to be understood as a homeostatic process that provides a countermeasure to stress.

As used herein, the term "stress response pathway" is to be understood as the form of the stress response that has a specific function in the organism, such as DNA repair. Stress response pathways are embodied in expressed molecules (i.e., SR biomarkers.)

As used herein, the term "universal stress response pathway" or simply "SR pathway" is to be understood as a form of stress response to most stressors, in most organisms. Functional activation of these SR pathways generates reproducible patterns of expressed molecules.

As used herein, the term "SR biomarker" is to be understood as an expressed molecule known to be or suspected of being associated with activation of a SR pathway.

As used herein, the term "SR biomarker profile" is a multi-dimensional pattern of data whose components are at least two SR biomarker scores for individual SR biomarkers across a SR biomarker panel.

TABLE 1

SR biomarkers monitor ten principal cellular stress responses.

| SR | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 |   |   |   | + | + |   | + | + | + | + | + | + | + |   |   |   | + | + | + |   |
| 2 |   |   |   |   | + |   |   |   | + | + |   | + | + |   | + |   | + | + |   |   |
| 3 |   |   |   |   |   |   |   |   | + | + |   | + | + | + | + | + | + | + |   |   |
| 4 |   | + | + |   |   | + |   |   |   |   |   | + |   |   |   | + | + |   |   |   |
| 5 |   |   |   |   |   |   | + |   |   |   |   |   |   |   |   | + | + |   |   | + |
| 6 | + |   | + | + | + | + | + | + | + | + | + | + | + | + | + | + | + | + | + | + |
| 7 |   | + | + | + | + | + | + | + | + |   |   | + | + |   |   | + | + | + |   |   |
| 8 | + |   |   | + |   |   | + | + | + |   | + |   | + | + | + | + |   |   | + | + |
| 9 | + | + |   | + |   | + | + | + | + |   | + | + | + | + | + | + | + | + | + | + |
| 10 |   |   |   |   |   |   |   | + |   |   |   |   | + |   |   |   |   |   |   |   |

| SR | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| 1 | + |   |   | + | + |   |   | + | + |   |   | + |   | + |   | + | + |   |   |   |
| 2 |   |   |   |   | + |   |   |   | + |   |   |   |   |   |   |   |   |   |   |   |
| 3 | + |   |   |   |   |   |   |   |   |   |   |   |   |   |   |   |   |   |   |   |
| 4 |   |   |   |   |   | + |   |   |   |   |   |   |   |   |   | + | + |   | + |   |
| 5 |   | + | + | + | + |   | + |   | + |   | + |   | + | + | + | + |   |   |   |   |
| 6 | + | + | + | + | + | + | + | + | + | + | + | + | + | + | + | + | + | + | + | + |
| 7 |   |   |   | + | + | + | + | + | + | + | + | + | + | + |   |   | + | + |   |   |
| 8 |   | + | + | + | + | + |   |   | + | + | + | + | + | + | + | + | + |   |   | + |
| 9 | + | + | + | + | + | + | + |   | + | + | + | + | + | + | + | + | + | + |   | + |
| 10 |   | + | + |   |   | + |   |   | + |   |   |   |   | + | + | + | + | + |   |   |

SRP biomarkers 1-40: beta-endorphin, caspase 8, cyclin D, Cox-2, CYP450, cytochrome c, EGFR, ferritin, glucocorticoid receptor, Grp58, Grp75, GSTp, Hsp25/27, Hsp40, Hsp60, Hsp70, Hsp90, HSF1, HO-1, IL-1 beta, IL-6, IL-8, IL-10, laminin, leptin receptor, metallothionein, Mekk-1, Mek-1, NADPH-CYP450 reductase, iNOS, Fos, Jun, serotonin receptor, serotonin, Substance P, SOD Mn, SOD Cu/Zn, TGFbeta, p53, vasoactive intestinal peptide.
SR, stress responses 1-10: redox control, cellular detoxification Phase I and II, chaperoning, DNA repair, cellular adhesion and motility, cell growth and energy metabolism, apoptosis, neuro-endocrine signaling, immunological activation, microbial activation.

As used herein, the term "SR pathway profile" is a multi-dimensional pattern of data representing at least two SR pathways. The components are functions of SR biomarker scores related to the individual SR pathways. The functions yield one-dimensional data points that provide simple-to-use indices of activation levels for the individual pathways.

As used herein, the term "stress response profiling" refers to constructing either or both SR pathway profiles or SR biomarker profiles from SR biomarker assays.

As used herein, the term "SR biomarker panel" is to be understood as at least two SR biomarkers that as a group provide enhanced information about stress responses than single SR biomarkers.

As used herein, the term "SR biomarker panel score" or "panel score" is to be understood as a one-dimensional data point calculated as the average of SR biomarker scores across a SR biomarker panel.

As used herein, the term "SR biomarker score" is to be understood as a normalized and optionally log-transformed measurement of a SR biomarker.

As used herein, the term "measurement" of a SR biomarker is to be understood as a quantitative or qualitative determination of the SR biomarker's expression level in a sample from an organism.

As used herein, the term "individual SR biomarker assay" or "SR biomarker assay" is to be understood as an assay of individual SR biomarkers.

As used herein, the term "combined SR biomarker assay" is to be understood as an assay that yields measurements representative of the combined expression levels for a panel of SR biomarkers.

The homeostatic processes monitored by SRP biomarkers regulate general stress responses, basic body functions and physical vital signs (body temperature, heart rate HR, blood pressure BP, respiratory rate). These homeostatic processes include redox control, cellular detoxification, chaperoning, DNA repair, cellular adhesion and motility, cell growth, apoptosis, neuron-endocrine signaling, immunity, and microbial activation.

Redox Control (1).

This pathway regulates levels of reactive oxygen and nitrogen species (superoxide, nitric oxide, carbon monoxide) through free radical scavenging proteins such as superoxide dismutases. Free radicals are essential cellular mediators but when in excess, they cause cellular dysfunction through damaging lipids, proteins, DNA and membrane integrity.

Cellular Detoxification (2).

Cellular detoxification provides a defense against chemical threats to cellular integrity. Phase I detoxification is a cytochrome P450 driven process for metabolizing a wide variety of endogenous metabolites (e.g. fatty acids, steroids) and foreign substances (drugs, alcohol, pesticides and hydrocarbons). Phase II is based on the glutathione metabolism and provides cellular resistance to oxidants, hydrocarbons and heavy metals.

Chaperoning (3).

Chaperones fold newly synthesized polypeptides and denatured proteins and for prevent uncontrolled protein aggregation. Chaperoning involves hundreds of "client" proteins and therefore has a key role in multiple biological functions including cellular protection, metabolism, growth, the development of multicellular organisms and molecular evolution. Excessive chaperoning facilitates disease by folding "wrong" clients such as the diphtheria toxin or mutant p53 that are cytotoxic or cause cancer.

DNA Repair (4).

DNA damage is ubiquitous and therefore the stability of the genome is under a continuous surveillance by multiple DNA repair mechanisms. DNA lesions are produced during transcription and replication, and by metabolic and immunity by-products (e.g. free radicals produced during aerobic respiration and by immune cells killing bacteria). DNA can be also damaged by environmental mutagens such as oxidants, heavy metals, radiation and viruses. The DNA repair pathway regulates multiple stages and mechanisms of DNA repair, and is closely linked with cell cycle control and apoptosis.

Cellular Adhesion and Motility (5).

This pathway monitors cellular interactions with the extracellular matrix and also changes in cytoskeletal matrix such as centrioles, kinetosomes and other microtubule organizing centers. These processes are essential for cellular survival, growth, metabolism and motility, and also for the formation of microbial biofilms and microbial-host interactions.

Cell Growth (6).

In multicellular organisms, cell cycle progression is strongly regulated during the development and modulated by growth factors (mitogens), disease and environmental stress. In mature tissues, most cells do not divide. Cycling cells in tissues are typically somatic stem cells involved in normal tissue turnover (e.g the germinal layer of the skin). Cell cycling is typically arrested in starved cells and in cells with DNA or mitochondrial damage. Increased cell growth occurs during immune responses, wound healing and regeneration of tissues damaged by environmental stress, toxins, disease or infection. Uncontrolled, excessive cell growth is found in cancer.

Cell Death (7).

The programmed cell death (apoptosis) "recycles" cellular components and prevents the release of toxins from dying cells, as happens during necrotic cell death. In animal tissues, apoptosis is increased in areas of tissue remodeling and wound healing, and during aging. During a disease, apoptosis can be increased within the diseased tissue (e.g. psoriatic skin lesions) and/or in remote tissues and biofluids (e.g. HIV Tat protein is a soluble mediator that triggers apoptosis in uninfected lymphocytes). Apoptosis can be also triggered by environmental stressors that cause mitochondrial damage (e.g. oxidative stress and uv light).

Neuro-Endocrine Signaling (8).

This pathway is crucial for regulating physiological homeostasis and behavioral regulation in animals including simple invertebrates. It involves a large number of mediators (hormones, neuropeptides, neurotransmitters) and cellular receptors produced by specialized tissues (glands and neural tissues), and also locally in peripheral tissues (e.g. skin and gut). In vertebrates, two signaling mechanisms provide initial responses to stress: the limbic hypothalamic-pituitary-adrenal (LHPA) axis that involves glucocorticoids (e.g. Cortisol) and the sympathetic nervous system activation via catecholamines. However, chronic stress also activates signaling of pain and anxiety, energy balance, metabolism, respiration, circulation and reproduction. Neuro-endocrine and immune signaling are integrated through common mediators and provide coordinated responses to environmental stress and disease.

Immunity (9).

Immunity provides a systemic defense against biological threats to organism's integrity such as injuries, tumors and disease-causing microorganisms. Innate immunity provides a nonspecific defense through soluble mediators (e.g. chemokines, agglutinins) and specialized cells (e.g. macrophages) that circulate through the organism and inactivate parasitic microorganisms, engulf apoptotic cell debris and kill infected and tumor cells. Innate immunity is found in protists, animals and plants. Vertebrates use innate immunity during the initial phases of stress response because it takes several days to activate specific immunity that provides threat-specific antibodies and lymphoid cells. Immune regulation is mediated through numerous signaling proteins called cytokines or interleukins. Increased immunity can be beneficial (e.g. short-term immune activation that removes a bacterial infection) or harmful (e.g. chronic inflammation and autoimmunity increase physiological stress through oxidative stress and apoptosis).

Microbial Activation (10).

This pathway monitors the activation of stress responses in microorganisms (bacteria, fungi, viruses), and signaling between microorganisms and host cells. Commensal microbial biofilms are an integral part of animal and plant bodies and contribute to physiological homeostasis. In animals, microbial biofilms are primarily associated with the inner and the outer body surfaces (the mucosal epithelium and the skin). Therefore microbial biofilms are sensitive both to environmental stressors (e.g. uv light) as well as to micro-environmental conditions in host tissues and body fluids (e.g. oxidative stress). During physiological stress, increased signaling between microbial biofilms and host cells promotes protection of the organism through modulating host's stress responses. For example, signaling by gastrointestinal microflora modulates levels of proteins with key roles in redox control, cellular detoxification, chaperoning, cell growth, apoptosis and immunity such as metallothionein, Hsp25, ferritin, p53, TGF beta, IL-8 and IL-10. When pathogenic microorganisms invade animals or plants, their stress responses are elevated, which in turn increases stress responses in the host (bacterial heat shock proteins are animal superantigens). Disease-causing microorganisms also release soluble mediators that trigger cellular stress and activate multiple stress response pathways in infected as well as remote host tissues (e.g. HIV Tat protein).

Stress Response (SR) Biomarkers

Activation of SR pathways by stressors results in a pattern of expressed molecules such as genes, proteins, metabolites and lipids, referred to herein as "SR biomarkers. Accordingly, each of these biomarkers is said to be "associated with" one or more SR pathways. Measuring the levels of these SR biomarkers provides useful information about the biological effects of stressors. Preferably, the SR biomarkers are expressed molecules such as proteins or fragments thereof, so long as the fragment is capable of being recognized in an SR biomarker assay with the same sensitivity as the entire protein.

Preferred SR biomarkers and their known associations with SR pathways are listed in Table 2. Additional SR Biomarkers and some but not all of their known associations with SR pathways are listed in Table 3.

TABLE 2

SR Biomarkers: Association with SR Pathways and Expression in Taxonomic Groups of Organisms

| # | SR biomarker | Abbreviated name | Expression | | | | | SR pathways | | | | | | | | | |
|---|---|---|---|---|---|---|---|---|---|---|---|---|---|---|---|---|---|
| | | | A | B | C | D | E | 1 | 2 | 3 | 4 | 5 | 6 | 7 | 8 | 9 | 10 |
| 1 | Beta-endorphin | Endorphin | + | + | + | | | 0 | 0 | 0 | 0 | 0 | 1 | 0 | 1 | 1 | 0 |
| 2 | Caspase8 | Caspase 8 | + | + | + | | | 0 | 0 | 0 | 1 | 0 | 0 | 1 | 0 | 1 | 0 |
| 3 | Cyclin D1 | Cyclin | + | + | + | | | 0 | 0 | 0 | 1 | 0 | 1 | 1 | 0 | 0 | 0 |
| 4 | Cyclooxygenase 2 | Cox-2 | + | + | | | | 1 | 0 | 0 | 0 | 0 | 1 | 1 | 1 | 1 | 0 |
| 5 | Cytochrome P 450 | CYP450 | + | + | + | + | + | 1 | 1 | 0 | 0 | 0 | 1 | 1 | 0 | 0 | 0 |
| 6 | Cytoplasmic cytochrome c | Cytc | + | + | | | | 0 | 0 | 0 | 1 | 0 | 1 | 0 | 1 | 0 | 0 |
| 7 | Epidermal growth factor receptor | EGFR | + | + | + | | | 1 | 0 | 0 | 0 | 1 | 1 | 1 | 1 | 1 | 0 |
| 8 | Ferritin | Ferritin | + | + | + | + | + | 1 | 0 | 0 | 0 | 0 | 1 | 1 | 1 | 1 | 1 |
| 9 | Glucocorticoid receptor | GR | + | | | | | 1 | 1 | 0 | 0 | 0 | 1 | 1 | 1 | 1 | 0 |
| 10 | Glucose regulated protein Grp58 | Grp58 | + | + | | | | 1 | 1 | 1 | 0 | 0 | 1 | 0 | 0 | 0 | 0 |
| 11 | Glucose regulated protein Grp75 | Grp75 | + | + | + | + | + | 1 | 0 | 1 | 0 | 0 | 1 | 0 | 1 | 1 | 0 |
| 12 | Glutathione-S-transferase p | GST | + | + | + | + | + | 1 | 1 | 0 | 1 | 0 | 1 | 1 | 0 | 1 | 0 |
| 13 | Heat shock protein 25/27 | Hsp25/27 | + | + | + | + | + | 1 | 1 | 1 | 0 | 0 | 1 | 1 | 1 | 1 | 1 |
| 14 | Heat shock protein 40 | Hsp40 | + | + | + | + | + | 0 | 0 | 1 | 0 | 0 | 1 | 0 | 1 | 1 | 0 |
| 15 | Heat shock protein 60 | Hsp60 | + | + | + | + | + | 0 | 1 | 1 | 0 | 0 | 1 | 0 | 1 | 1 | 0 |
| 16 | Heat shock protein 90 | Hsp90 | + | + | + | + | + | 1 | 1 | 1 | 1 | 1 | 1 | 1 | 1 | 1 | 0 |
| 17 | Heat shock transcription factor HSF-1 | HSF-1 | + | + | + | + | + | 1 | 1 | 1 | 0 | 0 | 1 | 1 | 0 | 1 | 0 |
| 18 | Heme oxygenase-1 | HO-1 | + | + | | | | 1 | 0 | 0 | 0 | 0 | 1 | 1 | 1 | 1 | 0 |
| 19 | Interleukin IL-1beta | IL-1 | + | + | | | | 0 | 0 | 0 | 0 | 1 | 1 | 0 | 1 | 1 | 0 |
| 20 | Interleukin IL-6 | IL-6 | + | + | + | | | 1 | 0 | 1 | 0 | 0 | 1 | 0 | 0 | 1 | 0 |
| 21 | Interleukin IL-8 | IL-8 | + | + | | | | 0 | 0 | 0 | 0 | 1 | 1 | 0 | 1 | 1 | 1 |
| 22 | Interleukin IL-10 | IL-10 | + | | | | | 0 | 0 | 0 | 0 | 1 | 1 | 0 | 1 | 1 | 1 |
| 23 | Interleukin IL-12 | IL-12 | + | | | | | 0 | 0 | 0 | 0 | 1 | 1 | 0 | 1 | 1 | 0 |
| 24 | Laminin | Laminin | + | + | | | | 1 | 1 | 0 | 0 | 1 | 1 | 1 | 1 | 1 | 0 |
| 25 | Leptin receptor | ObR | + | | | | | 0 | 0 | 0 | 0 | 0 | 1 | 1 | 1 | 1 | 0 |
| 26 | Metallothionein | MT | + | + | + | + | + | 1 | 0 | 0 | 1 | 0 | 1 | | 1 | 1 | 1 |
| 27 | Stress-activated MAP kinase Mekk-1 | Mekk-1 | + | + | + | + | + | 0 | 0 | 0 | 0 | 1 | 1 | | 0 | 1 | 1 |
| 28 | Mitogen activated MAP kinase Mek-1 | Mek-1 | + | + | + | + | + | 0 | 0 | 0 | 1 | 1 | 1 | | 1 | 1 | 0 |
| 29 | NADPH-cytochrome P 450 reductase | CYP red | + | + | + | | + | 1 | 1 | 0 | 0 | 1 | 1 | | 1 | 1 | 0 |
| 30 | Nitric oxide synthase II, inducible | iNOS | + | + | + | | + | 1 | 0 | 0 | 0 | 0 | 1 | 1 | 1 | 1 | 1 |
| 31 | Proto-oncogene c-Fos protein | Fos | + | + | + | | | 0 | 0 | 0 | in | 1 | 1 | 1 | 1 | 1 | 0 |
| 32 | Proto-oncogene c-Jun protein | Jun | + | + | + | | + | 0 | 0 | 0 | in | 0 | 1 | 1 | 1 | 1 | 0 |
| 33 | Serotonin receptor | 5HT R | + | + | + | | + | 0 | 0 | 0 | 0 | 0 | 1 | 1 | 1 | 1 | 0 |
| 34 | Serotonin | 5HT | + | + | + | | | 0 | 0 | 0 | 0 | 1 | 1 | 0 | 1 | 1 | 0 |
| 35 | Substance P | Substance P | + | + | | | | 0 | 0 | 0 | 0 | 1 | 1 | 0 | 1 | 1 | 0 |
| 36 | Superoxide dismutase Mn | SOD Mn | + | + | + | + | + | 1 | 0 | 0 | 1 | 1 | 1 | 0 | 1 | 1 | 1 |
| 37 | Superoxide dismutase Cu/Zn | SOD Cu/Zn | + | + | + | + | + | 1 | 0 | 0 | 1 | 0 | 1 | 0 | 1 | 1 | 1 |
| 38 | Transforming growth factors beta-1,2,3 | TGF | + | + | + | | + | 0 | 0 | 0 | 0 | 0 | 1 | 1 | 0 | 1 | 1 |

TABLE 2-continued

SR Biomarkers: Association with SR Pathways and Expression in Taxonomic Groups of Organisms

| # | SR biomarker | Abbreviated name | Expression | | | | | SR pathways | | | | | | | | | |
|---|---|---|---|---|---|---|---|---|---|---|---|---|---|---|---|---|---|
| | | | A | B | C | D | E | 1 | 2 | 3 | 4 | 5 | 6 | 7 | 8 | 9 | 10 |
| 39 | Tumor suppressor p53 | p53 | + | + | + | | | 0 | 0 | 0 | 1 | 0 | 1 | 1 | 0 | 0 | 1 |
| 40 | Vasoactive intestinal peptide | VIP | + | + | | | | 0 | 0 | 0 | 0 | 0 | 1 | 0 | 1 | 1 | 0 |

TABLE 3

SR Biomarkers: Association with SR Pathways

| # | SR biomarker | Abbreviated name | SR pathways | | | | | | | | | |
|---|---|---|---|---|---|---|---|---|---|---|---|---|
| | | | 1 | 2 | 3 | 4 | 5 | 6 | 7 | 8 | 9 | 10 |
| 41 | Heat shock protein 70 | Hsp70 | | | + | + | + | + | | + | | |
| 42 | Matrix metalloproteinase 9 | MMP | | | | | + | + | | + | | |
| 43 | Aldose reductase | ALR | + | + | + | | | | | | + | |
| 44 | Apoptosis signal-regulating kinase 1 | ASK | | | | | | | + | | | |
| 45 | Aquaporin 5 | AQP | + | + | + | | | | | | | |
| 46 | Betaine GABA transporter 1 | BGT | + | + | + | | + | | | | + | |
| 47 | SAPK | SAPK | | | | | + | + | | | | |
| 48 | Caspase recruitment domain protein 9 | CARD | | | | | | | + | | | |
| 49 | P38 MAPK | p38 | | | | | | + | | + | | |
| 50 | Peripheral benzodiazepine receptor | PBR | | | | | | + | + | + | + | + |
| 51 | Salivary alpha-amylase | SAA | | | | | | | + | | | |
| 52 | GroEL | GroEL | | | | + | | | | | + | |
| 53 | Superoxide dismutase EC | SOD EC | + | | | | + | | | | + | |
| 54 | Cell adhesion molecules | V-CAM, I-CAM | | | | | + | | | + | | |
| 55 | Monocyte chemotactic protein 1 | MCP | | | | | + | | | + | | |
| 56 | Catalase | Cat | + | | | | | | | | | |
| 57 | Hypoxia induced factor 1 alpha | HIF-1 | + | | | | | | | | | |
| 58 | Glutathion peroxidase | GSHPx | | | + | | | | | | | |
| 59 | Carbonic anhydrase | CAA | + | | | | | | + | | | |
| 60 | Ornithine decarboxylase | ORD | + | | | | | | | | | |
| 61 | Vasoendothelial growth factor | VEGF | + | | | | | + | | | | |
| 62 | Erythropoietin | EPO | + | | | | + | + | | | | |
| 63 | Melatonin | Melatonin | | | | | | + | | + | | |
| 64 | Thyroid-stimulating hormone receptor | TSHR | | | | | | + | | | | |
| 65 | Methenyl-tetrahydro-folate reductase | MTHFR | | | | | | + | | | | |
| 66 | Oxytocin | Oxytocin | | | | | | | + | | | |
| 67 | Thromboxane synthase 1 | TBXAS1 | | | + | | | + | | + | | |
| 68 | C-reactive protein | CRP | | | | | | | | + | | |
| 69 | TNF-alpha | TNF | | | | | | | | + | | |
| 70 | Apolipoproteins A and B | apo | | | + | | | + | | + | + | |
| 71 | Toll-like receptor | TLR | | | | | | | | + | + | |
| 72 | TspO protein | TspO | | | | | | | | | + | |
| 73 | Bacterial trehalose synthase | Tre-6P | | | | + | | | | | + | |
| 74 | Bacterial Sigma S factor | RpoS | | | | | | | | | + | |
| 75 | Protease DegP | DegP | | | | | | | | | + | |
| 76 | Superoxide dismutase Fe | SOD Fe | + | | | | | | | | + | + |
| 77 | Glutathione reductase A | gorA | | + | | | | | | | + | |
| 78 | Ferric uptake regulator | fur | + | | | | | + | | | | |
| 79 | Multidrug efflux pump | acf | | | + | | | | | | + | |
| 80 | Sigma-B factor | Sigma B | | | | | | | | | + | |
| 81 | DNA-binding protein stationary phase | dps | | | | | | | | | + | |
| 82 | DnaJ | DnaJ | | | | + | | | | | + | |
| 83 | GroES | GroES | | | | + | | | | | + | |
| 84 | 8-hydroxy-deoxyguanosine | 8-OH-dG | | | | | + | | | | | |
| 85 | 8-hydroxy-guanine | 8-OH-G | | | | | + | | | | | |
| 86 | DNA damage binding protein-2 | DDB2 | | | | | + | | | | | |
| 87 | Xeroderma pigmentosum (XP) C protein | XPC | | | | | + | | | | | |
| 88 | DNA glycosylase OGG1 | OGG1 | | | | | + | | | | | |
| 89 | pyrimidine-base DNA glycosylases | NEIL | | | | | + | | | | | |
| 90 | uracil DNA glycosyiase | UNG | | | | | + | | | | | |
| 91 | thymidine DNA glycosyiase | TDG | | | | | + | | | | | |
| 92 | DNA glycosylase | MTH1 | | | | | + | | | | | |
| 93 | Apurinic/Apyrimidinic endonuclease | APE | | | | | + | | | | | |
| 94 | MSH-2 | MSH-2 | | | | | + | + | + | | | |
| 95 | MLH-1 | MLH-1 | | | | | + | + | + | | | |
| 96 | Senescence-associated beta-qalactosidase | SA-beta-gal | | | | | + | + | + | | | |
| 97 | P21 | p21 | | | | | + | + | + | | | |

The relationship between each individual stressor and the ten SR pathways, and thus the SR biomarkers associated therewith, may not always be known, especially since the effects of many stressors on particular SR pathways is not yet well studied. For example, the effects of bird flu virus, engineered nanoparticles, and effects of deep space and deep sea or other extreme environments on each individual SR pathway may not be completely elucidated.

However, most SR biomarkers associated with the 10 SR pathways are useful targets in assays to analyze the effects of both known and unknown stressors, such as environmental stressors and/or diseases-related stressors. Accordingly, SR biomarkers associated with SR pathways are suitable targets for studying the effects of unknown stressors because they provide a response-oriented detection strategy that does not require prior knowledge of the stressor.

SR Biomarkers associated with the SR pathways are also suitable targets in studying the effects of complex stressors, some of which may be known and others of which may be unknown. These complex, or "combined" stressors, are common in real-life scenarios, and may include multiple known and unknown adverse conditions. Global warming, ozone holes, human effects on wildlife, urban pollution, natural and industrial disasters, poverty and war are examples of complex, combined stressors.

2. Dehydration

Dehydration is a water and electrolyte disorder that can severely affect human performance and health[18-21]. Preventable dehydration affects over 90 million people in the US and the costs exceed 10 billion annually for unnecessary hospitalizations and avoidable complications[18-55]. 3% dehydration (i.e., the loss of 3% total body water) is a critical end-point for dehydration diagnostics in field settings because it has measurable negative health consequences but it can be simply treated by oral rehydration[19,21,26,38,56-57]. 3% dehydration can be caused by sweating during strenuous physical work with restricted fluid intake or by extremes of temperature, humidity or altitude[19,21,29-30,58]. This type of dehydration frequently affects soldiers, athletes, construction workers, policemen and firefighters[21,24,26,28,30,44,53,59-63]. Acute dehydration due to gastroenteritis is frequent in children[34-36,39-42,46]. Chronic dehydration associated with oral disease is a common side-effect of cancer therapy or diuretics in diabetic and dialysis patients[31-33,45]. Elderly are at a greater risk for dehydration because the mechanism controlling thirst becomes less sensitive with age, and dehydration occurs more rapidly due to a lower water content in the aging body[25,47,49,51,64]. Many patients in the terminal phase of their illness experience dehydration due to a variety of causes related to their disease or treatment[32-33,48]. Dehydration is a major cause of mental deterioration and death in patients with Alzheimer's disease[25,64]. Life-threatening complications of dehydration include heat stroke, heat illness and hyponatremia due to over-aggressive rehydration[19-21,27-28,30,44,53,61,65].

Dehydration and hyponatremia are also common in patients with cystic fibrosis, kidney, heart and liver disease. Currently used methods for detecting dehydration are based on laboratory analysis of blood, urine, saliva and anthropometric indices such as body mass measurement. The gold standards for dehydration assessment are blood osmolality, body mass loss and TBW measurement using isotope dilution. However, no dehydration test is currently available for wellness and disease management in POC settings and in field conditions. A field-expedient dehydration test is also needed for monitoring the performance and health of military service members during training and deployment. Thus, there is an unmet need for non-invasive, rapid and accurate test for ≥3% dehydration that could be administered frequently to monitor the hydration status of at-risk individuals in field settings[18-19,24,44,59].

The dehydration test provided herein based on salivary SR biomarkers risk is radically different from current dehydration tests because it utilizes a new assay principle based on monitoring the physiological status of the patient. Recent studies indicate that the homeostatic processes monitored by SRP are also activated by dehydration. As shown in Table 4, SRP biomarkers are relevant to the sensing of water loss.

The assay principle was reduced to practice using an immunoassay of SR biomarkers that monitor the physiological status based on cellular stress responses in saliva. The saliva test is noninvasive, rapid and inexpensive. In contrast, the current dehydration tests monitor physical properties (e.g. osmolality) using blood or urine samples and expensive, time consuming laboratory assays.

TABLE 4

SRP biomarkers and molecular sensing of dehydration

| Cellular and molecular effects of dehydration | Homeostatic process | SRP |
| --- | --- | --- |
| Efflux of intracellular water | Chaperoning | + |
| Increased intracellular salinity | Redox control | + |
| Cell membrane distorsion | Cell adhesion and motility | + |
| Macromolecular crowding and denaturation | Chaperoning | + |
| Increased xenobiotics production | Cellular detoxification | + |
| Oxidative stress | Redox control | + |
| Cell growth arrest | Cell growth | + |
| Pro-apoptotic signalling | Apoptosis | + |
| Hormonal changes | Neuro-endocrine signaling | + |
| Inflammation | Immunity | + |
| Microbial biofilm changes | Microbial activation | + |

3. Occupational Stress

Some occupations involve exposures to complex environmental and psychological stressors, for example astronauts, pilots, divers, soldiers, police and haz-mat personnel. These occupational stressors are typically much more diverse and higher, compared to mainstream professions. Occupational stress can have adverse affects on health and performance and therefore needs to be monitored. Currently, there are no tests for occupational stress.

Occupational stressors can be physical (radiation, health, cold, altitude, gravity, vibrations), chemical (low air oxygen, toxic chemicals, micronutrient deficiency), biological (pathogens, injuries, jet leg, sleep deprivation) or psychological. Often, they involve undefined factors (e.g. outer space radiation, new pathogens).

There are two basic strategies for the detection of occupational stressors. The first one measures levels of potential health threats in the environment (e.g. levels of toxic chemicals). This approach is not suitable for synergistic stressors (e.g. a mixture of individually safe chemicals can be toxic), undefined agents (e.g. new types of pathogens or space radiation) and psychological stressors. The second strategy is based on measuring changes in health status during and after exposures. Currently used health monitors measure vital signs and perform metabolic blood/urine tests. These monitors are not sensitive to many occupational stressors and often they are invasive and not practical (e.g. a nest of wires for vital signs). New health tests under development measure molecular indicators of immunological status (e.g. cytokines and latent viruses in saliva and blood) or assess cognitive performance (e.g. specialized computer games).

The device of the invention offers a better solution for the assessment of complex occupational stressors than any of the current methods. The main advantages of SRP are broad-based sensitivity and new insights into the mechanism of stress. The SRP sensitivity allows an upstream, early detection strategy for a broad spectrum of occupational stressors. In contrast, current methods provide a downstream detection strategy focused on delayed effects. For example, SRP can measure molecular effects directly triggered by a radiation exposure such as increased free radical levels and protein denaturation. These effects precede immunological or cognitive changes by several hours to several days. The insights into the mechanism of occupational stress could be used for the development of countermeasures.

4. Male Fertility Test

Current male fertility tests use sperm counts and blood and saliva assays for reproductive hormones. Semen is a complex mucosal fluid with multiple cell types similar to saliva and milk. The device of the invention can be used to measure cellular stress in semen as an indicator of sperm health and a predictor of male fertility.

5. Embryonic Health Test

Current prenatal health tests use amniotic cultures to perform FISH assays for genetic abnormalities. SRP-based cellular stress test of the amniotic culture could serve as a new indicator of embryonic health and a predictor of prenatal health.

6. Oral Health Test

Current oral health tests use X rays and dental exams to detect periodontal disease, a serious chronic health problem. New expensive genetics tests are under development. SRP-based cellular stress in saliva could serve as a new indicator of oral health and a predictor of periodontal disease.

7. Saliva as a Diagnostics Sample

Oral diagnostics is a rapidly growing field that provides a convenient alternative to blood sampling for a rapidly expanding list of analytes and diseases, including an early test for a heart attack. It has previously been reported that SRP biomarkers in saliva were sensitive to chronic diseases and post-traumatic psychological stress. Saliva can be sampled simply and noninvasively. A typical saliva sample (10 drops, about 0.3 ml) contains about a half million of epithelial and white blood cells. Salivary cells may play a role in the cellular and molecular mechanism of oral disease transmission. It was also found that salivary cells express SRP biomarkers and that salivary SRP levels are strongly increased by stress.

Saliva diagnostics provides a noninvasive and safe alternative to blood or urine diagnostics[1-3]. The main challenge of using saliva as a diagnostic sample is the inherently low concentration of soluble biomarkers in the cell-free saliva fluid[1-3], which is the currently used method for saliva sampling[1-3]. We found that saliva contains a large number of cells (about $10^6$/ml) that contain clinically significant biomarkers[4-7]. Therefore, saliva samples that contain salivary cells provide a radically improved diagnostic sample for saliva diagnostics.

Saliva samples may be collected by the subject or may be collected by a passive method in which a health care worker or person other than the subject collects the sample. For example, unstimulated saliva samples maybe be collected having the subject collect saliva into a sterile container. Alternatively, saliva samples may be collected using a device such as a small oral brush by brushing teeth and gum surfaces on both sides of the mouth for about 20 seconds. To collect a larger volume of saliva, the brushing may be repeated using additional brushes. A comparison of saliva samples collected using self-brushing, and brushing performed by an assistant, showed that both methods yielded the same average sample volume and cellular composition. The passive saliva sampling method (brushing performed by an assistant) enables saliva diagnostics in subjects that cannot actively participate in active saliva sampling such as infants, elderly, unconscious patients or mentally ill patients. Currently, no other passive saliva collection methods were published that enable saliva diagnostics in these subjects.

The device for collecting salivary cells may consist of a disposable brush and a reusable handle. The brush is suitable for oral use. The brush may be used to collect saliva by brushing gums and teeth, and then may be used to process the saliva into smears on slides or lysates.

Methods that collect saliva samples containing salivary cells provide a radically improved diagnostic sample for saliva diagnostics because salivary cells contain clinically significant biomarkers (e.g. proteins and DNA)[4-7]. In contrast, current methods for saliva sampling collect cell-free saliva that has inherently low concentration of soluble biomarkers, which is the main challenge in using saliva as a diagnostic sample[1-3].

In one embodiment of the invention, there are provided reference reagents and materials for saliva diagnostics generated by inducing cellular stress in cultured normal salivary cells by in vitro treatment. Although as described below, the induction of proteomic biomarkers using 5 stressors is exemplified, the treatment principles could easily be adapted to protocols that use different stressors, or other stress markers such as mRNA, DNA, reporters or small molecules associated with the activation of SR pathways (see Table 1). Moreover, the method principles could be also easily adapted for other human cells that have a diagnostic value, e.g. white blood cells, and for diagnostic cells from animals, plants and microorganisms. Although the production of cell smears as reference materials is exemplified, the method principles could easily be adapted to the production of other types of reference materials and reagents such as protein lysates, mRNA lysates or cell-free saliva fluid.

Methods that induce cellular stress in cultured normal salivary cells by in vitro treatment provided novel reference reagents materials for saliva diagnostics such as salivary cell smears with normal and increased levels of salivary biomarkers. The in vitro production of reference reagents and materials was rapid, convenient and inexpensive. The new reference materials are radically different from current reference materials produced using cell-free saliva samples[1-3] collected from patients with and without specific medical conditions.

Also provided herein are methods for the development of salivary biomarker assays. In one example, the method uses reference reagents and materials prepared as described in Example 2. Two types of laboratory saliva immunoassays are exemplified, the immunocytochemical (ICC) assay and the ELISA assay. Together, these assays enable the development and validation of saliva biomarker panels because they provide complementary analysis of cell-associated (ICC) and soluble (ELISA) saliva biomarkers as described in Example 5. In addition, laboratory saliva ELISA assays are also useful as reference assays for the development of commercial saliva assays such as the lateral-flow immunoassay (LFIA) test strip. Although as described below, the development of saliva ICC and ELISA assays exemplified, the principles of the method could easily be adapted to developing other types of immunoassays such as LFIA, and to assays that measure other types of markers such as mRNA, DNA or small molecules. The method for developing new saliva assays using reference reagents and materials produced in vitro was rapid, convenient and inexpensive compared to currently used methods based on clinical saliva samples. Saliva assays produced by the new method use saliva samples that contain salivary cells and therefore the new assays are radically different from current saliva assays based on cell-free saliva samples[1-3].

Also provided are methods for measuring baseline concentrations of saliva biomarkers using two complementary assays, ICC for cell-associated biomarkers in saliva smears, and ELISA for soluble biomarkers in saliva lysates. In one example, the method uses reference reagents and materials prepared in vitro as described in Example 2. Biomarker baselines in normal saliva provide a useful benchmark the construction of biomarker panels for saliva diagnostics as described in Example 5. Although as described below, the baseline measurement of a protein biomarker using the ICC and ELISA assays is exemplified, the assay principles could easily be adapted to measure soluble protein markers using other assays such as the lateral-flow immunoassay, and other types of biomarkers such as mRNA, DNA or small molecules.

Also provided are methods for constructing a biomarker panel that is useful for salivary diagnostics of health disorders. Although as described below, panels of proteomic markers are exemplified, the same principle could easily be adapted to measure, for example, mRNA, DNA or small molecules, and to assess the diagnostic value of the saliva biomarker panel using other statistical methods than exemplified here. The new method is rapid, convenient and inexpensive because it uses reference reagents produced in vitro, compared to current methods that use reference reagents based on clinical saliva samples[1-3].

8. LFIA Biosensors

The first FDA-approved commercial oral biosensor broke the ground for a successful commercialization of oral diagnostics. This breakthrough test is ORAQUICK ADVANCE® RAPID HIV-1/2 ANTIBODY TEST produced by OraSure. The test is based on a mature biosensor technology, the lateral-flow immunoassay (LFIA). LFIA is rapidly expanding to provide a wide variety of POC and point-of-need tests for wellness (pregnancy and ovulation tests), public health (HIV and Hepatitis C tests) and forensics (drug and alcohol tests).

Figure 6:
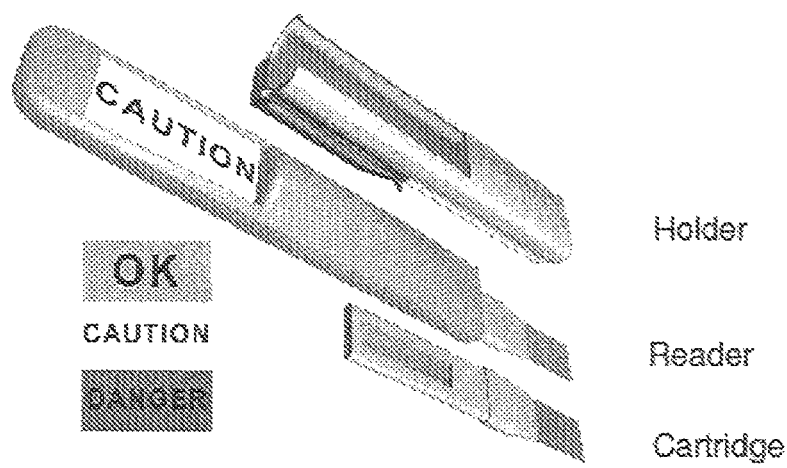
FIG. 6 shows an illustration of a rapid, hand-held test device for saliva biomarkers. The device consists of a disposable cartridge for uptake of saliva sample and reagent storage, and a reusable reader for signal detection and result display. The result indicates the presence of a saliva biomarker. The digital display window identifies results as normal (display reads "OK"), moderately abnormal (display reads "CAUTION") or highly abnormal (display reads "DANGER").
Figure 7:
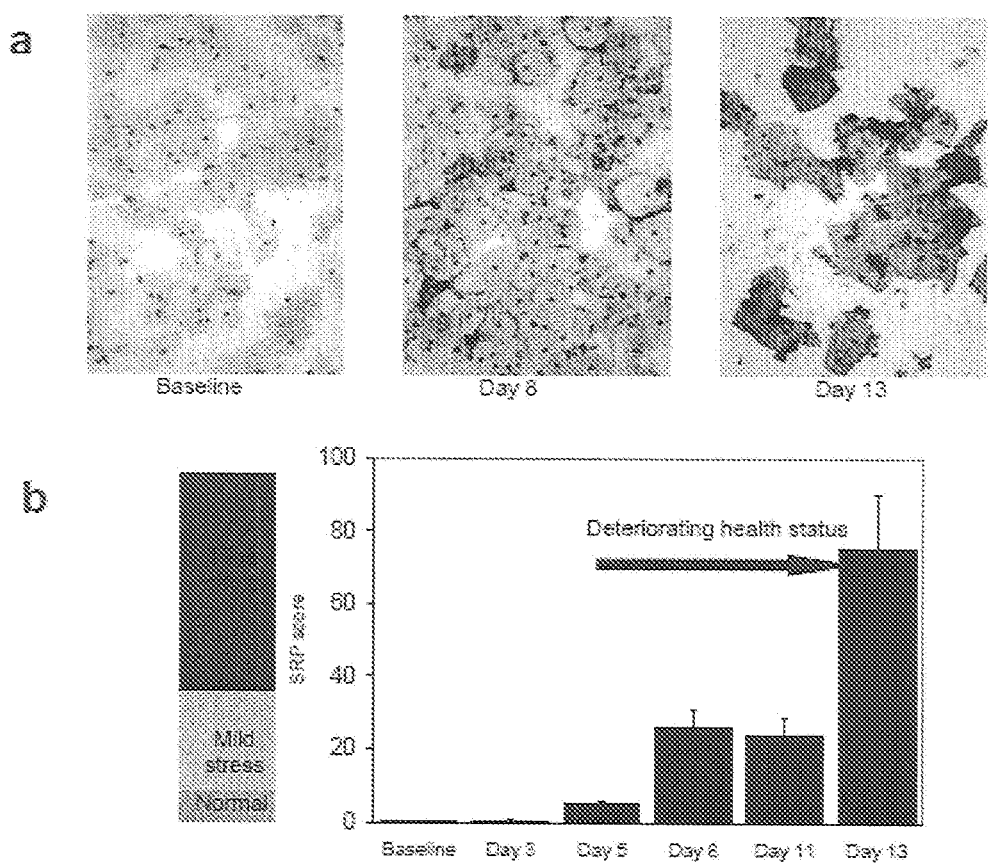
FIG. 7A shows images of multi-SRP staining of saliva cells.
FIG. 7B shows a plot of the SRP score calculated as the ratio between the average staining intensity across 900 saliva cells, and the maximum staining intensity value for saliva cells.

The present invention provides a simple analyzer that provides a quantitative measurement of physiological stress. Examples of the analyzer is shown in FIGS. 6 and 7. The analyzer consists of a reusable reader with a digital result display and disposable cartridges (test strips). Alternatively, the whole unit is disposable. The test result is a "stress number," or "SRP score," which is a quantitative indicator of the general stress level. A color-coded results window is used for simplified interpretation of the stress number: e.g. green for normal, yellow for mild/moderate and red for high stress levels (similar to a digital thermometer). If the stress number is above the normal range, a digital message prompts the user to obtain advanced analysis of their stress, and to seek medical advice.

In one embodiment of the analyzer device, there is provided a pen-size digital device consisting of a disposable teststrip, a reusable electronic reader and a clip-on holster. The user briefly puts the end of the test strip in the mouth to collect saliva and then inserts the test strip into the reader. In less than 3 minutes, the reader shows a digital stress measurement. A color guide shows whether results indicate normal health (green), a mild health problem (yellow) or serious health deterioration (red). Results from multiple tests are stored on board and can be wirelessly communicated to a remote care center. The device operates autonomously using small batteries that last for several weeks.

An advanced analyzer that provides quantitative and qualitative measurements of physiological stress is also provided in the present invention. The analyzer uses a disposable cartridge to perform a highly multiplexed immunoassay (10-40 individual biomarkers). Assay results are measured and processed using an opto-electronic reader. Test results are displayed digitally. The analyzer is equipped for data transfer (USB, bluetooth) to a web-based service (StressNet) that supports advanced analysis of test results. The analyzer can be a desktop device or a PDA-class handheld device.

The average SRP score is computed by the device based on measurements of the individual biomarkers and displayed in the results window at the end of the test. The average SRP score will be interpreted as a quantitative indicator of the general stress level, analogous to the "stress number" (combined SR biomarker score), since the average SRP score strongly correlated with combined SR biomarker scores in reference samples. If the general stress level is above the normal range, the user will be prompted to perform advanced analysis of his SRP profile using a web service. The software on the web service interprets the SRP profile and provides user-friendly results in the form of a short message. The message (1) describes the nature of personal stress, e.g. the % risk of specific health problem, (2) shows top three personal stress drivers, (3) recommends wellness products/services that are the best match for the personal stress drivers, and (4) directs the user to additional information.

9. Predictive Medical Diagnostics and Personalized Disease Management

Many health problems and diseases do not have a lab test that could provide early warnings before the onset of clinical symptoms. This is particularly true for mental diseases. Often, the earlier a disease is diagnosed, the more likely it is that it can be cured or successfully managed. Managing a disease, especially early in its course, may lower its impact on life or prevent or delay serious complications. Disease management strategy strongly depends on the ability to predict the severity of a disease, for example, differentiating metastatic cancer, Alzheimer's dementia, or kidney failure. Such predictive tests are currently unavailable.

Chronic diseases are associated with early physiological changes that might be detectable using SRP biomarkers in saliva. Early disease tests can be done based on stress-induced changes in microflora and mobile genetic elements (MGE). SRP profiles might reflect the course of a disease. For example, a metastatic cancer might have a different SRP profile than a non metastatic cancer because metastatic cells produce chemical compounds and biological interactions that are likely to affect stress responses in the normal cells and biofluids analyzed in SRP assays.

Methods: The SRP panel (40 or 41 biomarkers) is analyzed in samples from case/control subjects (cases represent a disease, e.g. breast cancer, BC). If SRP profiles unambiguously discriminate between BC and controls, the panel is minimized toward the smallest panel sufficient for the BC classification. Based on the preliminary data, the minimized panel will consist of 3-6 biomarkers. If SRP profiles from the original SRP panel do not discriminate BC, new biomarkers are added to the panel until the SRP profile can discriminate BC. The new biomarkers are selected using the SR pathway profile of BC determined by the original SRP panel. For example, if BC-related stress preferentially involves misfolded proteins, oxidative stress and changes in cell cycle and growth, then new biomarkers for these processes will be preferred. When SRP profile can discriminate BC, the biomarker panel will be minimized as described above. The minimized panel is detected using combined SR biomarkers ("multi-SRP assay'), if a combined score is sufficient for BC detection. Alternatively, the biomarkers in the minimized panel are measured individually if a SRP profile is needed for BC detection. A multi-SRP test or an assay for 3-6 individual SRP biomarkers will be implemented using the device of the invention.

10. Human Disease Research

The cellular and molecular mechanism of a disease (i.e. molecular pathogenesis) shows where and how the disease harms the body. Diseases perturb cellular and physiological homeostasis, and the perturbation pattern might be disease-specific and reproducible (i.e. a disease-specific stress signature). Disease countermeasures prevent, reduce or remove the disease-specific stress signature. Disease-specific stress signatures can be analyzed by SRP. This information can be used to guide the development of disease countermeasures: preventive treatments, diagnostics tests and therapeutic interventions. Molecular pathogenesis of most diseases remains elusive including the Spanish flu and AIDS. New molecular and bioinformatics tools are needed, in particular systems biology-based approaches such as SRP measurements using the device of the invention.

11. SRP Tests for Cancer

Oral Tests for Cancer Screening and Lab Tests for Cancer Diagnostics

Carcinomas of the skin, breast and prostate are among the most common human malignancies. Current diagnostic methods typically involve a series of tests. For example, a general screening test at POC is ordered by a family doctor during routine health testing (e.g. mammogram for BC). If this test is positive, the patient is referred to a Cancer Center. The Cancer Center surgeon performs a surgical biopsy that is examined by a cancer pathologist using morphological criteria (e.g. nuclear morphology, mitotic number) and molecular pathology (antibody staining or DNA probing). If the biopsy is considered positive (malignant growth), the patient is referred for additional surgery. The surgical specimen is analyzed by a pathologist to assess the tumor grade based on general grading scales (e.g. Gleason score for PC). New research in personalized medicine aims to delineate the molecular mechanism of individual tumors using gene arrays or antibody staining. Following radio- and chemotherapy, diagnostic tests based on surgical biopsies and blood assays (not available for most cancers; PSA is used for PC) and are used to identify metastatic cancer. Many cancer survivors suffer chronic pain and mental health problems for which there are no objective tests. A related health problem is caregiver stress.

Tests for SRP are applicable across the cancer management continuum—examples are listed below.

(1) Cancer screening for noninvasive early detection of cancer.

Rapid oral test for BC and PC: a disposable LFIA. The test is based on a multi-SRP assay optimized for a particular cancer (a yes/no result). Some versions can discriminate metastatic cancer.

Rapid semen test for PC: a disposable LFIA. The test is based on a multi-SRP assay optimized for PC (a yes/no result). Some versions can discriminate metastatic cancer.

Lab test for cervical cancer. The test is based on a multi-SRP staining kit optimized for cervical cancer detection in a standard cervical smear. Some versions can discriminate metastatic cancer. The kit is used to stain a duplicate cervical smear in parallel with the standard PAP test and provide a yes/no result. The SRP test could be used as a decision support for PAP (increased accuracy of cancer prediction) and ultimately replace the PAP test. The accuracy of PAP would be improved in two ways. First, positively staining cells with abnormal morphology (i.e. PAP test reading made easier, faster, more accurate). Second, positively staining pre-cancerous cells with a normal morphology that cannot be detected by PAP. The replacement could happen fast if the SRP test would provide an outstanding benefit over PAP, e.g. discriminating metastatic cancer.

(2) Cancer diagnosis for early detection of metastasis.

Lab test for a particular cancer. The test is based on a multi-SRP staining kit optimized for the particular cancer and corresponding tissue type. The kit is used to stain the biopsy tissue and also the surgically removed tissue (tumor and adjacent tissue). The test can discriminate metastatic cancer.

A staining kit for measuring individual SRP biomarkers. Results (SRP profiles) interpreted using the computer software. Results show a match with reference SRP profiles (i.e. discriminate between not cancer, cancer, metastatic cancer). The results indicate the molecular mechanisms of the particular cancer (pathway profile). This information can be useful as a guide for personalized therapy.

(3) Cancer survivors for improved quality of life.

Rapid oral test for cancer-related psycho-biological stress in survivors.

Rapid oral test for cancer care giver stress.

12. Early PTSD Test

A large number of military service members suffer from PTSD and traumatic brain injury (TBI). These diseases are complex psycho-biological disorders that are hard to detect and quantify, particularly in early stages, before they can be assessed using standard psychological/neurological tests. These standard tests require highly trained medical personnel, therefore they are not practical for POC or at home monitoring. New tests for PTSD (under commercial development) include assays for saliva cortisol and saliva alpha-amylase (SAA). These analytes are biomarkers for HPA and sympathetic nervous system pathways. SRP covers these pathways and many more pathways that are likely to be activated by psycho-biological stress. Cortisol and SAA are also likely to give false positive signals because they are increased by routine stressors.

13. Early Alzheimer's Test

Alzheimer's disease is the most common cause of dementia. The device of the invention can be used for rapid oral test for early Alzheimer's. The test is based on SRP biomarkers optimized for the disease.

14. Early Autism Test

Autism (ASD) is a rapidly growing health problem for kids in the US. Current goal for autism diagnostics is a test suitable for infants (<3 yrs). Oral SRP test using the device of the invention would be more suitable than tests currently under development.

15. Early Kidney Stones Test

A July 08 report predicted a sharp rise in kidney stones-related health problems in the US due to a higher incidence of dehydration caused by global warming. The device of the invention can be used for a rapid oral test for early detection of kidney stones. The test is based on SRP biomarkers optimized for kidney stones.

16. Early Kidney Disease Test

Chronic kidney diseases (CKD) are on a rise worldwide and early detection is essential for CKD management. The device of the invention can be used for a rapid oral test for early detection of CKD. The test is based on SRP biomarkers optimized for CKD.

17. Animal Wellness and Food Safety

There is a worldwide increase in emerging diseases and environmental stressors related to factory farming, genetic modifications of crops and life stock, antibiotics overuse, human impact on wildlife and global warming. This increase might be responsible for increased morbidity and mortality of domesticated and wild animals, wild species extinctions, and collapses of the US lobster fishery and the honeybee industry. Early detection of new diseases and environmental stressors is essential for public health, agricultural safety and wildlife protection and management.

Factory farms keep animals in unhealthy conditions. Many animals are diseased and exposed to environmental stressors (crowding, injuries, antibiotics etc). Organic farms are more likely to have less stressed animals. Besides the ethical objections, products from stressed animals are likely to have a lower nutrient value and might even present a health threat for consumers because stressed animals are likely to be ill and the product might transmit diseases (e.g. mad cow disease), or might contain metabolites that can cause health disorders because they deregulate human cell function. For example, human metabolic disorders triggered by animal hormones or immune disorders triggered by animal stress proteins. Currently, there is no objective test that regulators or consumers can use to assess whether a farm product is from a healthy or from a stressed animal. Such test would help consumers to choose products from minimally stressed animals, and help regulators to search for unhealthy farm conditions.

A related issue is the safety of animal foods (pet food, farm feed). If animal foods contain parts of diseased animals, it might transmit the disease (e.g. BSE) or cause other types of health disorders.

The device of the invention can be used for SRP analysis of animal cells and tissues related to disease, injury, environmental stress, and animal health and product safety, including:

1. Stress tests for animals and animal products (milk, egg).

The tests use the device of the invention modified for the use with animal samples.

Saliva test for companion animals (dog, cat, horse); one smart test device with species-specific cartridges or sample-specific tests.

Milk test: a health test for dairy animals & milk quality test. Could be made as an attachment for a milking machine or equipment for milk quality test. SRP assay of milk cells and fluids similar to the saliva SRP assay.

Egg test: a health test for poultry & egg quality test.

Male fertility test.

Urine test (a litter test for cats; farm animals).

Fish test. Fish biopsy or a surrogate small fish or invertebrate living in the same habitat.

Shellfish test.

Beehive wellness test. The honeybee keeping industry has nearly collapsed due to an unknown health threat (environmental factors or disease).

2. Stress test for meat.

Cattle, pork, poultry, fish.

3. Stress test for animal food.

Multi-SRP test that shows whether pet food and farm feed products contain parts of stressed animals.

4. Stress test for sentinel organisms.

Multi-SRP test of sentinel animals and wild animals found sick or dead of unknown causes. Increased stress indicates exposure to an emerging/occult disease or environmental stressors. For example, chickens are currently used as sentinels for infectious bird diseases.

18. Agricultural Safety

Plant diseases have increased worldwide possibly due to unsustainable farming practices such as the widespread use of chemical fertilizers, pesticides and genetically modified plants, and global warming. Integrated monitoring of soil/plant/crop health could improve wellness of farm crops, garden plants and house plants, and provide decision support for the protection and management of wild plant ecosystems such as forests and wetlands. Healthy crop plants are likely to produce crops that are more nutritious and case less health problems such as food allergies. Currently, there is no objective test that regulators or consumers can use to assess whether a crop (grains, fruits etc) is from a healthy or from a stressed plant. Such test would help consumers to choose products from minimally stressed plants, and help regulators to search for unhealthy crop conditions.

Soil fertility correlates with the microbial richness of the soil, which is naturally low in some soils (e.g. tropical soil) and becomes depleted by agricultural use. Currently, there is a strong global interest in the restoration of soil fertility due to two factors: a rapidly growing need for increased food production, and soil loss & depletion driven by global warming. However, there is no direct test for monitoring the wellness of soil microflora (the indirect test is the assessment of soil fertility based on crop yield and quality). There are traditional soil probiotics such as compost or charcoal but no new, scientifically-based products that would rationally reduce stress in soil microbial systems.

There is an urgent need for a new technology that could assess and improve soil fertility and crop health. The device of the invention to assess SRP technology meets these specifications.

19. Plant Disease and Food Research

Multi-SRP and SRP assays using the device of the invention can be adapted for soil and plant samples.

20. Stress Tests for Soil, Plants and Crops

Different soil samples can be analyzed using the device of the invention with the SRP biomarker panel optimized for soil microorganisms. Another SRP panel can be optimized for plants, focusing on stress markers for plant organelles (chloroplasts, mitochondria), comensal microorganisms (same as soil) plus stress markers that are in all species (e.g. Hsp60/GroES or SOD). Candidate samples for plants include: roots, leaves, stems, sap. Samples for crops include: grains, fruits.

21. Environmental Safety

Water Safety

Water safety affects public health, aquaculture, agriculture and natural aquatic ecosystems. Standard methods for assessing water safety are based on measuring several chemical and physical parameters (e.g. pH, temperature and turbidity), and levels of specific microbial and chemical contaminants. In England, a traditional method for water safety is still used: the health condition of fish in the water (how many, how fast they swim past the observatory). Frogs are also traditionally used as sentinel organisms for freshwater health. Since these methods do not provide early warnings of declining water safety, new methods are currently being developed and tested. Several new methods measure the health condition of native aquatic microorganisms. One method uses an infrared motility monitor. Another one, AquaSentinel, developed at the Oak Ridge National Labs, uses a fluorescence reader to measure changes in algal bioluminescence.

The device of the invention can be used to provide SRP-based tests for water safety, and provides several advantages such as: applicability to both fresh water and seawater, broad-based sensitivity to changes in chemical, physical, biological water parameters including parameters that are not measured by current sensors such as new types of air pollutants or agricultural run-off chemicals, early warning of incipient water health deterioration (molecular stress responses precede changes in an algal fluorescent signature or motility), detection of emerging pathogens and biotoxins in aquaculture water that could be directly correlated to fish health, signature can be used to diagnose the nature of the water stress and to recommended countermeasures and used to monitor the effectiveness of countermeasures in restoring water health.

Background—Air Safety

Microbial biosensors for airborne toxins have been introduced recently. Typically, these are genetically engineered bacteria or recombinant flies with a read-out gene (e.g. lux) linked to one of several particular toxin-sensitive genes (hsp70, DNA J). The disadvantage is that recombinant organisms have to be manufactured for the biosensor operation, and the small set of recombinant sensor genes in the biosensor might not be sensitive to the large and diverse spectrum of environmental stressors that affect people. The device of the invention can be used to provide SRP-based tests for air safety.

22. Space Technology

Key areas in space biology research that are useful with the device of the invention include: diagnostic and therapeutic technologies for astronaut health. The goal is to identify health risks of space flight and develop countermeasures to reduce those risks. The device of the invention can also be used for fundamental space biology investigations in microbial, plant and cell biology and animal physiology, i.e. how life responds to gravity and space environments. Additionally, the device of the invention can be used to detecting life's signatures for future planetary missions to Mars, Europa and Titan.

23. Detection of Life's Signatures

Stress responses (SR) are universally present in all organisms on Earth. Responses to universal stressors are essential for life in general and could be used in the search for life. The universal stressors are physical-chemical gradients or agents commonly present in planetary geological environments (e.g. electromagnetic radiation, radioactivity, temperature, gravity, heavy metals, water, $CO_2$). Universal stressors are also generated by general biological processes such as self-organization, electron transfer and metabolism (e.g. heat, entropy and free radicals). Different biological systems might use very different biochemical structures for SR but the different biochemical structures are likely to have the same or similar physical-chemical functions. These general functions can be deduced through comparative study of biochemical structures that are commonly used for SR by terrestrial organisms. Components of the general physical-chemical SR functions are used as biomarkers for life.

For example, free oxygen and nitrogen radicals (RONS) are universal stressors produced by solar radiation as well as a by-product of electron transfer and metabolic reactions. RONS cause harm to all living systems through damage to macromolecular structures and shifts in redox balance. All terrestrial organisms have SR against RONS. Most prokaryotes and eukaryotes use control RONS using superoxide dismutases (SOD). The physical-chemical function of SOD is carried out by the metal moiety of SOD, which contains an antioxidant heavy metal (Fe, Mn, Cu, Zn). These and similar (Ni, Co) metals are candidate biomarkers for biological anti-RONS responses.

Another universal stressor is water loss (desiccation). Most prokaryotes and eukaryotes have a SR for adapting to life without water (anhydrobiosis). If there was or is life on Mars, it had to deal with periodical desiccation as well. The physical-chemical functions underlying the anhydrobiosis SR are candidate markers for life detection.

Bacterial and eukaryotic cells use organic osmolytics to cope with anhydrobiosis (glutamate, proline, glycerol, sucrose, trehalose, sorbitol, myo-inositol and glycine betaine). The physical-chemical principle of the osmolytic compounds is structure-making (cosmotropic) function: they organize the water structure (hydrogen bonding) which is essential for structural integrity of biological membranes and biopolymers (e.g. proteins). The known organic osmolytics listed above, and other cosmotropic compounds, are candidate biomarkers for biological response to osmotic stress and for anhydrobiosis.

24. Monitoring HIV/AIDS Risk and Treatment Outcome

HIV/AIDS is a priority public health condition[67]. There are about 1.1 million HIV infected people in the U.S. and 56,300 new HIV infections annually[67]. Currently, two lab tests (CD4 count and viral load) are the gold standards for assessing AIDS risk and guiding cART[68-69]. CD4 counts 350 (recently increased to 500) and 200 cells/mm$^3$ are standard actionable thresholds for guiding cART[68]. The CD4 test is expensive, invasive, time consuming, requires specialized equipment, highly trained personnel and has to be repeated every 3-4 months. Thus, there is an unmet need for an affordable POC test for AIDS risk and guiding cART[69].

In one embodiment of the invention there is provided a rapid saliva test for predicting AIDS risk treatment outcome that has been developed using following steps: (1) A candidate panel of 52 SR markers (see Tables 2 and 3) was constructed using methods from Example 5. (2) The initial clinical validation of the panel used methods from Example 5 and saliva samples from HIV/AIDS patients (n=100) with CD4 counts >500, 200-500 and <200 cells/mm$^3$. The AIDS risk test based on salivary SR biomarkers is radically different from current tests for the condition because it utilizes a new assay principle based on monitoring the physiological status of the patient. The assay principle was reduced to practice using an immunoassay of SR biomarkers that monitor the physiological status based on cellular stress responses in saliva. The saliva test is noninvasive, rapid and inexpensive. In contrast, current tests for AIDS prognostication monitor the immunologic, virologic or genetic status of the patient using blood samples and expensive laboratory assays[68-69,72].

The saliva test for AIDS prognostication has potential to provide significant benefits for public health and substantial healthcare savings in several ways: (1) Accelerating HIV/AIDS care and slowing the spread of HIV: Two rapid oral tests could be administered during routine healthcare screening, an HIV diagnostics test followed by the saliva test in order to inform patients about their HIV status and AIDS risk in a single office visit so that they could receive care immediately. Pain-free, affordable oral testing is likely to increase the number of HIV/AIDS patients connected to care and fewer people will be exposed to HIV: 54-70% of new HIV infections in USA are caused by people who are not treated and engage in risky behaviors because they do not know that they are HIV infected[67]. (2) Moving AIDS monitoring from lab to point-of-care will greatly improve the delivery of clinical care and medications in resource-limited settings where the standard tests for AIDS risk are not affordable and costly cART drugs are delivered inefficiently, without lab tests[69,74]. (3) Enabling personalized HIV medicine: frequent affordable testing of cART efficacy will facilitate designing and modifying cART for individual patients, which has potential to improve treatment outcomes and decrease clinical costs[72].

The following examples are intended to illustrate but not limit the invention.

EXAMPLES

Example 1

Collection and Processing of Improved Saliva Samples for Saliva Diagnostics

This experiment provides an exemplary method for collecting and processing saliva samples that contain salivary cells. Although as described below, assays based on the collection of human unstimulated saliva by spitting or brushing are exemplified, the assay principles could easily be adapted to protocols that collect and process stimulated saliva samples, or use other devices and methods, or collect animal saliva.

Sample collection. Unstimulated saliva samples were collected from healthy volunteers (5 women, 5 men, 8-53 yrs old). The subjects were asked to brush teeth and have no food or beverage except water for 30 minutes (min) before the collection. Two collection methods were used: (1) Spit was collected into a sterile container such as the 50 ml Falcon tube. Subjects spit into the tube several times during about 15 minutes (min) until 3 to 6 ml of saliva was collected. During the collection, the tube was kept on ice. (2) A small oral brush described in FIG. 1 was used to collect saliva by brushing teeth and gum surfaces on both sides of the mouth for about 20 seconds. When a commercial oral brush (the PROX-ABRUSH Trav-ler, Sunstar Americas, Chicago, Ill.) was used for this collection method, the average collected saliva volume was 0.16±0.02 ml. To collect a larger volume of saliva, the brushing was repeated using additional brushes. A comparison of saliva samples collected using self-brushing, and brushing performed by an assistant, showed that both methods yielded the same average sample volume and cellular composition.

Sample quality tests: (1) The adequate pH (6-8) was assessed by spotting 5 μl of the spit on a pH test strip, or by pressing the tip of the gum brush on a pH strip. Samples tested so far (n>100) had pH=7.2±0.6. (2) The adequate cell count (epithelial cells and leukocytes) was assessed using one of the following methods. 1. Viable cell count. Saliva sample collected by spitting was mixed thoroughly using a sterile 1 ml pipette. Using a sterile pipette tip, 10 μl from the middle of the tube was transferred into a tube with 10 μl of 0.4% trypan blue in the phosphate saline buffer pH 7.60 (PBS), mixed using the pipette tip, stained for 10 minutes (min). 10 μl of the mixture was transferred into both chambers of a standard hemocytometer and viable cells (nucleated cells unstained by trypan) were counted using ×100 magnification. Adequate viable cell count was at least 0.2×10$^6$ cells/ml. 2. Total cell count. Saliva sample collected by spitting was mixed thoroughly using a sterile 1 ml pipette. Using a sterile pipette tip, 5 μl from the middle of the tube was smeared across a small square (about 1 cm$^2$) on a coated microscopy slide (a Silane Prep slide from Sigma, St. Louis, Mo.). Alternatively, saliva collected by the brush was smeared across about 1 cm length of the slide. Air dried saliva smears were fixed (1 dip in 2% formaline-1% acetic acid-80% ethanol followed by 10 dips in water) and stained using hematoxylin and eosin (H&E stain, Sigma): 10 dips in hematoxylin followed by 10 min in water, 10 dips in 80% ethanol, 10 dips in eosin, 10 dips in 95% ethanol, air dry, 2 dips in xylene, coverslip. Cells stained with H&E were counted at ×100 magnification. The adequate cell count was at least 2,500 cells per smear (>5×10$^5$ cells/ml). Normal saliva smears typically contained nucleated epithelial cells and leukocytes as well as about 10% of epithelial cells without nuclei. (3) The adequate cellular composition of the sample was determined based on microscopic inspection of the H&E saliva smear. A typical saliva sample collected by spitting had about 60% epithelial cells and 40% leukocytes (monocytes, lymphocytes and granulocytes). Brush-collected samples typically had about 50% epithelial cells and 50% leukocytes. In addition, all normal saliva samples also contained variable amounts of resident bacterial and fungal cells (about 10$^5$-10$^7$ microbial cells/ml). The salivary microbial cells were associated with the mammalian cells, or formed microbial clumps or were dispersed as single cells.

Salivary cell smears on microscopy slides ("smears"). Smears are useful for salivary diagnostics in multiple ways. They enable H&E analysis and the quantitative measurements of cell-associated molecular biomarkers (proteins, peptides, mRNA, DNA, small molecules such as eicosanoids, or reporters) in salivary epithelial cells, leukocytes and microbial cells. Proteomic markers and small molecules can be measured using the immunocytochemical staining ("the ICC assay") or by other assays such as reporter assays or in situ nucleic acid hybridization. Smears were prepared using following methods. 1. Saliva collected by spitting. The sample was thoroughly mixed in a tube using a 1 ml sterile pipette. Using a sterile pipette tip, 40 μl from the middle of the tube was transferred on a coated slide and the spot was immediately spread across the whole slide using the tip. The tip was tilted at a sharp angle to facilitate the spreading. In some experiments, smaller volumes of saliva were spread in separate areas of the slide to compare different saliva samples on the same slide (e.g. four smears, 10 μl each). 2. Samples collected using oral brush. Immediately after removing from the mouth, the brush was smeared across the length of a coated slide. The same brush was used to prepare additional slides (typically, 4 slides per brush). Additional brushes were used to collect more saliva and prepare a full set of slides for biomarker analysis (e.g. 25 slides were prepared using 7 brushes). Smears prepared sing the spit or brush methods were air dried at room temperature (RT) for at least 30 min, fixed in 10% normal buffered formalin for 10 min, followed by 3×5 min rinses in PBS, 5 min in water and 5 min each in 80%, 95% and absolute ethanol. Dry fixed slides were stored in a standard histology slide box at RT. The fixed slides were stable for over 3 years based on the ICC assay using control antibodies.

Salivary ICC assay. The main advantages of ICC are sensitivity (specific staining of single cells corresponding to 0.1-1 pg/ml antigen concentration) and specificity (each marker stains specific cell type and has a characteristic cellular localization). To demonstrate compatibility with ICC, representative saliva smears were stained with control antibodies. Positive control antibodies were specific for antigens consistently expressed by salivary epithelial cells or leukocytes. As positive controls, EMA (a membrane antigen on about 30% salivary epithelial cells; mouse IgG2a, 0.2 μg/ml, Biogenex, San Ramon, Calif.) and CD68 (a cytoplasmic antigen in salivary monocytes, B cells and neutrophils, mouse IgG1, 0.5 μg/ml, Dako, Carpenteria, Calif.) were used. Negative control antibodies were mouse monoclonal antibodies (Mab) and rabbit polyclonal antibodies (Pab) specific for irrelevant antigens that are not present in salivary cells. Negative controls matched the concentration, species and type of positive control antibodies and anti-biomarker antibodies. As negative controls, a mouse IgG1 Mab (anti-digoxigenin, 0.5 μg/ml, Santa Cruz Biotechnology, SCBT, Santa Cruz, Calif.) and a rabbit Pab (anti-Drosophila armadillo, 0.2 μg/ml, SCBT) was used. A new protocol was developed to enable ICC assay of saliva smears. Before staining, dry slides were scored with a diamond pen to outline sections for the application of different antibodies (typically 4 control antibodies were applied to one slide; in antibody titration experiments, 8 antibodies were applied to one slide). Assay steps: (1) Based on extensive testing, it was determined that commonly used antigen unmasking methods that use heat treatment (citrate or glycin buffers, 95-100° C. for 10-20 min) were not suitable for saliva smears because >80% cells fell off slides during the heat treatment. Therefore, a new method was developed for antigen unmasking in saliva smears: slides were placed in 20 mM citrate, 0.1 mM EDTA buffer (pH 3.0) at 37° C. for 60 min, followed by 5 min rinses in water and PBS pH 7.60. (2) Slides were blocked using PBS with 7% normal goat serum for 30 min. (3) Based on extensive testing (64 rabbit and goat Pabs, 25 mouse and rat Mabs), we determined that (i) Mabs (whole culture supernatants, ascites or purified immunoglobulins) and immunoaffinity-purified Pabs were suitable for salivary immunoassays whereas (ii) Pabs in the form of the whole serum (nonimmune serum or antiserum) or the immunoglobulin fraction of a whole serum, were unsuitable for salivary immunoassays because they contained antibodies that strongly stained 10-30% salivary microbial cells even when highly diluted (<10:1000). The anti-microbial affinity of whole serum has never been reported previously, probably because typical samples for immunoassays are sterile tissue culture cells, blood cells and fixed tissues that were stripped of resident microbes. Based on the results, only Mabs or affinity-purified Pabs were used for all saliva immunoassays (ICC or other assay formats). (3) Optimal concentrations of primary antibodies (the EMA, CD68, digoxigenin, armadillo antibodies) were diluted in PBS, pH 7.60 with 1% bovine serum albumin (BSA) and applied to individual sections on blocked slides after draining off the blocking solution and dividing the cell smear into fields by wiping between the outlined sections using a sharply folded paper tissue. The total antibody volume was 0.3 ml per slide. Afterwards, slides were placed in a humidified chamber at 4° C. for 16-20 hrs. (4) After 3×5 min rinse with PBS, a secondary antibody was applied for 90 minutes at RT (a biotinylated goat antibody against mouse and rabbit IgG, Biogenex, 1:20 in PBS-BSA), followed by 3×5 min rinse with PBS, enzymatic conjugate for 30 min at RT (a streptavidine-alkaline phosphatase conjugate, Biogenex, 1:20 in PBS-BSA), 3×5 min rinse with TBS (50 mM Tris, 150 mM NaCl, pH 7.60), chromogen (Fuchsin, Dako), 5 min water rinse, hematoxylin stain for 1 min, 15 min water rinse and two 5 min rinses with 95% ethanol. Air dried slides were rinsed in xylene and cover-slipped before a microscopic examination at ×100 magnification. (5) The staining intensity was quantified using computerized image analysis. 3 representative images were captured in each stained section and areas with at least 100 epithelial cells or leukocytes were outlined in each image. The mean optical density (MOD) in the outlined area, and the percent of the stained area (PA), were determined by applying a color file to the image. The same color file was applied to all images to ensure consistent MOD and PA measurements. The staining intensity (SI) was calculated as SI=MOD×PA. The mean SI was calculated for 3 images per stain. To determine the reproducibility of the assays, the mean SI was measured in 12 duplicate stains produced in the same and consecutive assay runs. The measurements were compared using linear regression analysis to calculate 95% confidence interval for the mean of differences. The coefficient of variation (CV) was 9.8%, demonstrating that the measurement was reproducible. Results of the control staining showed critical parameters for the ICC assay: sensitivity 0.1-1 pg/ml (based on the EMA antigen concentration), specificity (no staining with negative control antibodies), intra- and inter-assay reproducibility (<10% CV for the mean SI measurements).

Saliva protein lysates. The lysates enable detecting protein, peptide and small molecule biomarkers present is cell-free saliva and released from solubilized salivary cells. Lysates can be analyzed using ELISA, protein blots, mass spectrophotometry, chromatography or other types of assays. As explained in the ICC assay protocol above, antibodies suitable for saliva immunoassays are Mabs or immunoaffinity-purified Pabs. Lysates were prepared using two methods. (1) Spit-based samples: 1 ml of a 2× concentrated lysis buffer (LB) was added per 1 ml saliva; the sample was thoroughly mixed using a sterile 1 ml pipette and kept on ice for 30 min. The final concentrations in the lysate were 1 mM EDTA, 1 mM PMSF, 1 mg/ml N-ethylmaleimide, 0.02 mg/ml ovatrypsin inhibitor, 0.1 mg/ml aprotinin, 6 mg/ml 4-aminobenzamidine dichloride and a cocktail of mammalian phosphatase inhibitors from Sigma diluted in PBS. (2) Saliva was collected using the oral brush (FIG. 1) as described above. Immediately after the collection, the brush was removed from the handle and suspended in 2×LB. Four brushes (the PROXABRUSH Trav-ler, Sunstar Americas) were mixed with 0.3 ml of the LB in one microcentrifuge tube by swirling the brushes in the buffer for 30 seconds. The brush was kept in the buffer on ice for 30 min, and then removed. After lysis, insoluble material was removed by centrifugation at 12,000 rpm and the supernatant was transferred to a new tube and immediately frozen at −80° C.

Saliva ELISA. The ELISA assay complements the ICC assay of biomarkers in salivary cells by measuring soluble biomarkers. The main benefits of ELISA are sensitivity to 1 pg/ml biomarker concentrations, consistent high throughput and reliable metrics (pg/ml concentration) that clearly show the success of clinical diagnostic studies. To demonstrate compatibility with ELISA, we used a multiplexed MultiBead ELISA (Inflammatory Panel, Assay Designs, Ann Arbor, Mich.) to measure 8 control proteins (IL-1beta, IL-4, IL-6, IL-8, IFN-gamma, TNF-alpha) and small molecules (eicosanoids PGE2 and TXB2) with known concentrations in normal saliva[8-10]. Calibration curves for the analytes were constructed using serial dilutions of purified standards first in buffer (PBS-BSA) and then saliva matrix (the saliva protein lysate described above, a pool from several subjects). The assay was optimized to reach benchmark values of critical assay parameters: limit of detection at 1-10 pg/ml, linear range 10 pg-10 ng/ml, recovery (assay interferents), specificity (no signal with irrelevant purified antigens), intra- and inter-assay reproducibility (<10% CV for the mean measurements of duplicate samples in the same and in consecutive assay runs). The optimized assay was used to measure the 8 control analytes in normal saliva lysates from individual subjects.

Saliva DNA lysates. These lysates enable measuring DNA released from solubilized salivary cells. DNA prepared from the lysates can be analyzed using PCR, DNA blots or other types of DNA assays. Assays of saliva DNA have potentially wide applications in human and animal diagnostics including pharmacogenomics (individualized testing of drug safety and efficacy), testing for genetic disorders (disease prognostics), paternity and forensics. Although as described below, a protocol for DNA preparation is exemplified, the protocol principles could easily be adapted to protocols that prepare RNA. Saliva DNA lysates were prepared from saliva collected by spitting in a tube or by oral brushing as described above. The objective was to develop a simple method that could be used in field conditions using reagents and lysates that are stable at RT, and can be later processed in a laboratory to prepare DNA suitable for PCR amplification. Six such methods were developed: (1) 0.1 ml of a 5× concentrated lysis buffer (LB) was added to 0.5 ml spit in a sterile tube, the sample was thoroughly mixed using a sterile 1 ml pipette or vigorous shaking. Final concentrations in the lysate were 10 mM Tris-HCl, 10 mM EDTA, 0.1% sodium dodecyl sulphate (SDS). Fresh concentrated Proteinase K (PK, Qiagen, Valencia, Calif.) was added to 10 µg/ml final concentration. The lysate was incubated at 50° C. for 1 hr, boiled for 3 min, 25 µl of 5M NaCl was added to 0.2 M final concentration, the sample was mixed with 1 ml absolute ethanol, incubated at RT for 20 min, centrifuged at 14,000 rpm for 10 min, the pellet was rinsed with 70% ethanol, air dried and dissolved in 50 µl of 10 mM Tris-1 mM EDTA buffer pH 7.60 (TE). (2) Same as Method 1 but the LB contained diluted PK and was stored at RT for 2 days before use. (3) Same as Methods 1 or 2 but after boiling, 50 µl of 5M iced potassium acetate (pH 4.8) was added, the sample was mixed thoroughly, iced for 30 min, centrifuged at 14,000 rpm for 15 min, the supernatant was transferred to a new tube, mixed with 1 ml of absolute ethanol, incubated at RT for 20 min, centrifuged at 14,000 rpm for 10 min, the pellet was rinsed with 70% ethanol, air dried and dissolved in 50 µl of TE. (4) Same as Methods 1-3 but the lysate was incubated at RT for 18 hrs instead of at 50° C. for 1 hr. (5) 0.5 ml of spit was mixed thoroughly with 0.1 ml of a concentrated lysis buffer by vortexing or vigorous shaking. Final concentrations in the lysate were: 50 mM NaOH, 10 mM EDTA and 0.025% SDS, and the pH was about 12. The lysate was stored at RT for 8 days without additional mixing. On day 9, the lysate was boiled for 10 min, iced to RT, neutralized to pH 7.8 by adding 5 µl of 2M Tris-HCl pH 7.0 and 25 µl of 1M HCl. The neutralized lysate contained 50 mM NaCl. Insoluble material was pelleted by centrifugation at 14,000 rpm for 5 min, the supernatant was transferred to a new tube, 15 µl of 5M NaCl was added to final concentration of 0.2 M, the lysate was mixed with 1 ml of absolute ethanol, incubated at RT for 20 min, centrifuged at 14,000 rpm for 10 min, the pellet was rinsed with 70% ethanol, air dried and dissolved in 50 µl of TE. (6) Same as Methods 1-5 but saliva was collected using an oral brush (FIG. 1) as described above. Immediately after the collection, the brush was removed from the handle and suspended in LB. Four brushes (PROXABRUSH Trav-ler, Sunstar Americas) were mixed with 0.1 ml of 5×LB in one microcentrifuge tube by vortexing or by 10× swirling the brushes in the buffer. To estimate the DNA concentration and the molecular weight (MW), 5 µl each of a DNA standard (HyperLadder I, Bioline, Taunton, Mass.) and the saliva DNA were analyzed using a standards 0.7% agarose TBE gel with 0.5 µg/ml ethidium bromide. The average yield per 1 ml saliva was: 3±1 µg of high MW DNA (>20 kbp) for Methods using PK (1-4) and 1.5±0.5 µg of mediate-low MW DNA (1-20 kbp) for Methods using NaOH (5). To show compatibility with PCR, a 500 bp fragment of the human IFN-beta gene was amplified in the different saliva DNA preparations using following primers: 5' ATG ACC AAC AAG TGT CTC CTC CAA A and 5' GTT TCG GAG GTA ACC TGT AAG TCT G, and standard hot-start reaction conditions using 1.5 mM $MgCl_2$, 40 Cycles: 94° C. (45 sec); 60° C. (60 sec); 72° C. (60 sec), then final extension at 72° C. (10 min). The PCR product and a DNA standard were visualized using a standard 2% agarose gel stained with ethidium bromide.

Salivary cells. Live, fixed or permeabilized salivary cells are useful for salivary diagnostics by enabling the detection of molecular biomarkers using flow cytometry (FCM) or immunofluorescence assays. As explained in the ICC assay protocol above, antibodies suitable for saliva immunoassays are Mabs or immunoaffinity-purified Pabs. Salivary cells were prepared using the following procedure: Spit was diluted 1:1 with a staining buffer (SB: phosphate buffered saline, pH 7.6, 2% BSA, 0.1% azide) and centrifuged at 300 g for 5 min. Brush-collected salivary cells were released into SB (10-30 brushes submerged in 1 ml SB, 5 min on ice on a rocker), and centrifuged as above. The cell pellet was suspended in a minimal volume of SB (e.g. 0.1 ml), 5 µl were removed to perform a cell count, and to determine >90% cell viability using trypan blue exclusion as described above. The average yield was about $6 \times 10^5$ mammalian cells/ml spit, and about $3 \times 10^4$ cells/brush. To demonstrate compatibility with FCM analysis, duplicate samples of salivary cells were stained with control antibodies using a standard protocol for staining of live cells: The cell suspension was diluted to get a final cell concentration of about $10^6$ cells/ml, incubated with anti-Fc receptor antibody (CD32, SCBT, 1 mg/ml, 10 min), divided into staining samples in microcentrifuge tubes (at least 1×10⁵ cells/sample), centrifuged at 300 g for 5 min at 4° C., resuspended in 0.1 ml with a FITC-labeled primary antibody diluted in SB (1:5 diluted CD68-FITC and normal mouse IgG$_1$-FITC, SCBT), mixed and incubated on ice in dark for 30 min, rinsed 3× with SB and transferred into a Falcon 2052 tube with 0.4 ml SB before FACS analysis.

Example 2

Production of Reference Reagents and Materials for Salivary Diagnostics

This experiment provides an exemplary method for the production of novel reference reagents and materials for saliva diagnostics by inducing cellular stress in cultured normal salivary cells by in vitro treatment.

Preparation of stressed salivary cells. Saliva samples (6 ml) were simultaneously collected from 3 healthy volunteers (1 man and 2 women, 19-52 years old) using the spit method from Example 1. The acceptability of the samples was immediately evaluated using a pH test and H&E stain as described in Example 1. The samples were combined into a "Normal (N) pool". A portion of the N pool was processed into smears and or lysates using protocols from Example 1 (e.g. 3 ml was processed into 75 smears). The remaining N pool (15 ml) was divided into 5 cultures: (3 ml saliva, ~1×10⁶ viable cells/culture). The cultures were maintained in sterile Petri dishes (polystyrene, 60 mm×15 mm, Sigma) in a standard cell culture incubator at 37° C. for 18 hrs without adding culture medium. The cultures contained whole saliva with all normal salivary cell types: epithelial cells, monocytes, B and T lymphocytes, granulocytes, fungi and bacteria. Each culture was treated by a different environmental stressor: (1) Hypersalinity was induced by adding 150 mM NaCl and incubation for 18 hrs, as previously used for cultured kidney cells[11]. (2) Oxidative stress was induced by adding 0.01% azide and 0.2 M ethanol and incubation for 18 hrs. (3) Heat shock was induced by incubation at 44° C. for 2 hrs followed by incubation at 37° C. for 16 hrs. Similar conditions were previously used to heat shock HeLa cells[12]. (4) Cold shock was induced by freezing saliva at −80° C. for 2 hrs (3 sterile cryotubes, 1 ml saliva/tube), thawing on ice by adding 1 volume of warm growth medium (RPMI with 20% fetal calf serum), transfer into a sterile Petri dish and incubation at 37° C. for 18 hrs. (5) Desiccation was induced by reducing the culture volume to 1 ml using progressive evaporation during 2 hrs, followed by 16 hr incubation at the same volume. A portion of each treated culture (1 ml from treatments 1-3, 2 ml from treatment 4 and 0.3 ml from treatment 5) was processed individually as "Treated (T1-T5)". Remaining treated cultures were combined into a "Stressed (S) pool" (about 10 ml) before processing into smears on slides. The smears were produced using methods from Example 1.

Figure 2:
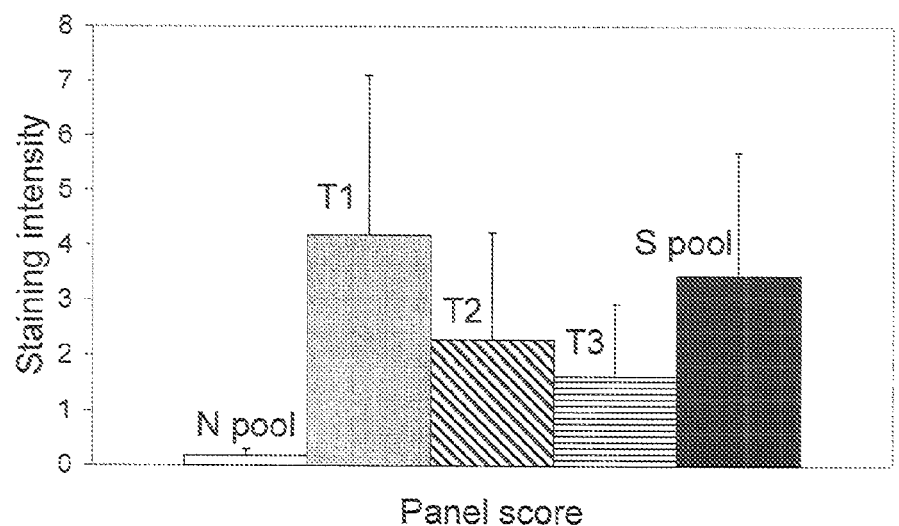
FIG. 2 shows a plot of the levels of stress response (SR) biomarkers in salivary cells treated with different environmental stressors. SR biomarkers were detected using enzymatic immunochemical staining assay with mouse and rabbit antibodies and a permanent color label. The staining intensity was measured in relative optical density units using image analysis. The y axis shows the average staining intensity for 40 SR biomarkers. Error bars show standard deviations of the average staining intensity. N pool, untreated salivary cells from three donors. Cultured cells from the N pool were treated by desiccation (T1), hypersalinity (T2) or heat shock (T3). S pool, cells combined after treatment of the N pool by desiccation, hypersalinity, heat shock, oxidative stress and freeze/thaw shock.

To determine if the treatments induced cellular stress, 40 SR markers were measured in smears of N pool, S pool and T1-T5 using the ICC assay protocol described in Example 1. The primary antibodies were a pool of antibodies against 40 SRP markers (see Table 2) and control antibodies were as described in Example 1. The treatment was considered successful if the average SR marker level was over 3 fold higher in treated saliva (T1-T5, S pool) than in the N pool, see FIG. 2.

Figure 3:
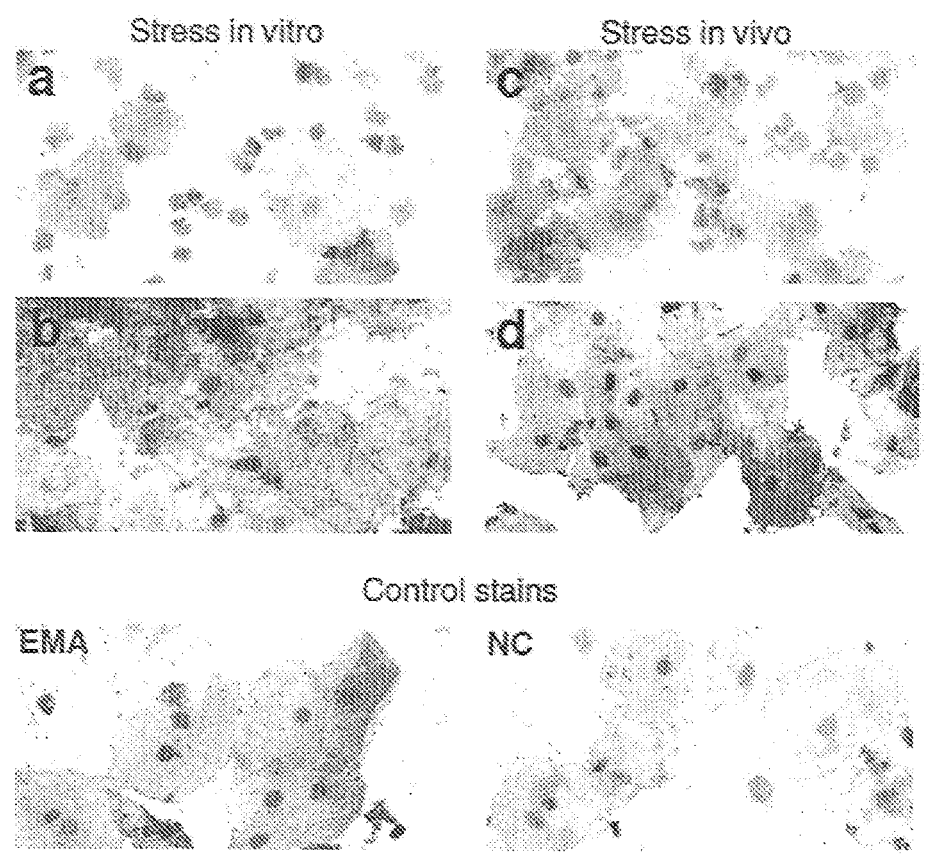
FIG. 3 shows cellular stress in saliva induced by treatment in vitro or by physiological stress in vivo. 40 SR biomarkers were detected in salivary cells using immunochemical staining with a color label. In cell images, the color is shown as stippling. a, N pool, normal saliva from 3 donors. b, S pool, cells combined after treatment by desiccation, hypersalinity, heat shock, oxidative stress and freeze/thaw shock. c, salivary cells from a healthy donor. d, saliva from the same donor during post-traumatic physiological stress. EMA, positive control staining of a cytoplasmic protein in salivary epithelial cells. NC, a negative staining control.
Figure 4:
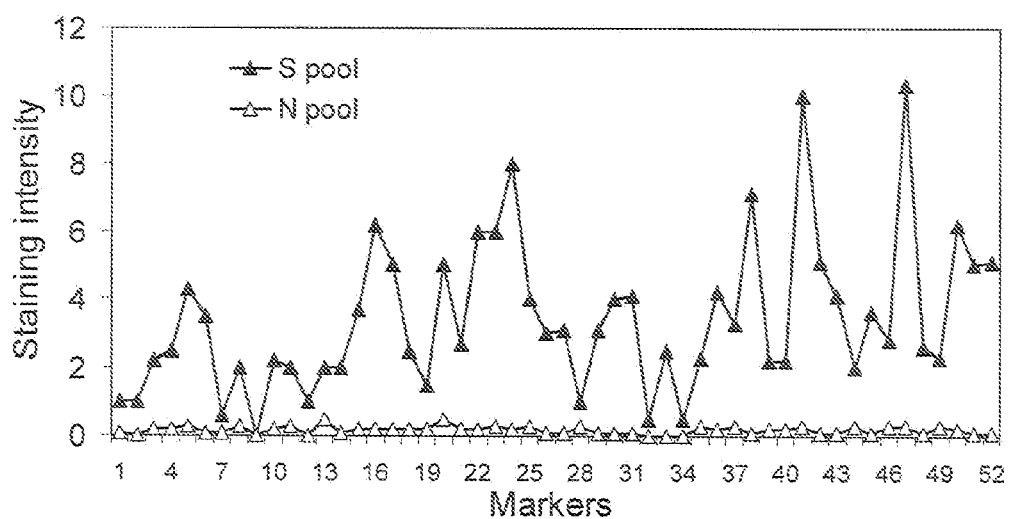
FIG. 4 shows a plot of shows levels of individual SR biomarkers before and after treatment with environmental stressors. 52 SR biomarkers were measured using immunochemical staining and image analysis. The y axis shows the average staining intensity for the 52 biomarkers. N pool, untreated salivary cells from three donors. S pool, cells combined after treatment by desiccation, hypersalinity, heat shock, oxidative stress and freeze/thaw shock.

Although stressed salivary cells can be prepared from using one donor and a single environmental stressor, the preferred method described above is based on the combination of saliva samples from several donors treated using 2 or more different environmental stressors. The preferred method produces a broad-based cellular stress in saliva, as salivary cells from different genetic backgrounds respond to the various stressors by activating multiple stress response pathways. The broad-based cellular stress results in altered levels of numerous biomarkers that are affected by cellular stress. The induced biomarkers are present both within salivary cells and also secreted into the culture medium. FIG. 3 documents that treatment of saliva cells by the preferred method increased levels of SR biomarkers more than 20-fold indicating a broad-based cellular stress. FIG. 4 shows that at least 50 individual SR markers were induced by the preferred method indicating broad-based activation of the 10 principal SR pathways monitored by the 40 markers (see Table 1).

Figure 5:
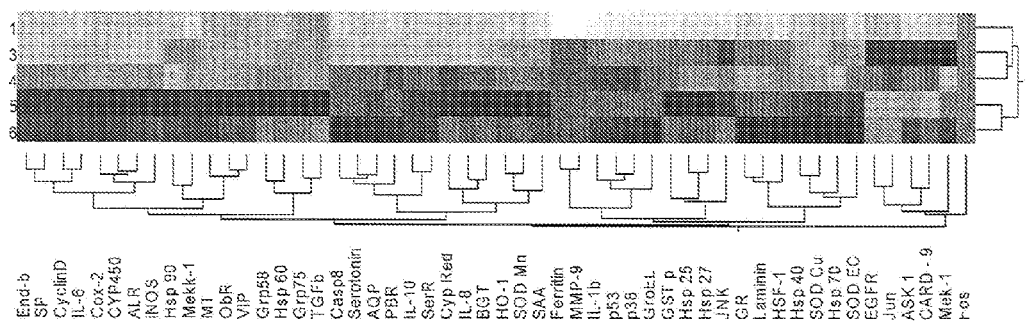
FIG. 5 shows expression profiles of SR biomarkers induced by treatment of salivary cells with different stressors. 52 SR biomarkers were measured using immunochemical staining and image analysis. The measurements were analyzed using hierarchic clustering to depict relatedness between profiles. The color scheme indicates biomarker levels. The lowest level is white, increased levels are gray to black. Similar profiles are in clusters with short dendrogram branches. N, untreated salivary cells from three donors. S, cells combined after treatment by desiccation, hypersalinity, heat shock, oxidative stress and freeze/thaw shock. T1a and T1b, desiccation, two subjects. T2, hypersalinity. T3, heat shock.

FIG. 5 shows that (i) the SR marker profile induced by desiccation was reproducible in salivary cells from different subjects, (ii) SR profiles discriminated between effects of desiccation, heat shock and hypersalinity and (iii) three SR markers were sufficient to discriminate between effects of desiccation and heat shock.

Broad-based cellular stress in saliva produced by the preferred method is directly relevant to clinical salivary diagnostics because a very similar broad-based cellular stress was found in saliva samples collected from subjects with disease or trauma, see FIGS. 3a-d.

The 40 SR markers were detected in volunteers with inflammatory conditions that commonly affect the oral cavity (gingivitis and periodontitis, n=2). These volunteers typically had about 5-10% higher concentration of salivary leukocytes. The average SR marker concentration was less than 1.1-fold higher in the saliva with inflammatory conditions than in saliva from subjects without the condition (n=10), which is a statistically insignificant. This result indicates that salivary diagnostics of disease or trauma is not affected by common oral inflammatory conditions.

Example 3

Development of Assays for Salivary Biomarkers

This experiment provides an exemplary method for the development of a salivary biomarker assay. The method uses reference reagents and materials prepared as described in Example 2. Two types of laboratory saliva immunoassays are exemplified, the immunocytochemical (ICC) assay and the ELISA assay.

The ICC assay. Methods in Example 2 were used to prepare reference slides for the assay: salivary cell smears of the N and S pools. The reference slides were first used to determine the optimal concentration of the tested anti-marker antibody. The reference slides were prepared using 20 µl of the N pool horizontally smeared across the top of the slide, and 20 µl of the S pool smeared across the bottom of the slide. Before staining, the slide was vertically divided into 4 sections by scoring the opposite side of the slide with a glass pen so that each section contained the N pool on the top and the S pool on the bottom. The sections were stained with 4 serial dilutions of the anti-marker antibody using the ICC staining protocol from Example 1. Parallel slides were stained with the control antibodies described in Example 1. The optimal concentration of the anti-marker antibody was identified based on the smallest detectable specific staining in the N pool, and the highest signal ratio between N and S pools. The sensitivity of the assay was shown based on the detection of single stained cells. The specificity of the assay was shown as the absence of staining with the negative control antibody. The reproducibility of the assay was shown as <10% CV for repeated measurements of the mean staining intensity in duplicate samples N and S pools in the same assay run and in 3 consecutive runs. Optimal concentrations of 52 SR markers determined using this method are in Table 5.

Using the validated ICC assay, the tested biomarker was measured in triplicate slides of the individual smears. Smears of the N pool and S pool were used as reference slides with normal and increased levels of saliva biomarkers. The mean

TABLE 5

Antibodies for the detection of SR biomarkers in salivary cells

| ANTIGEN | ANTIBODY | M | DF | ANTIGEN | ANTIBODY | M | DF |
|---|---|---|---|---|---|---|---|
| ASK-1 | AAP-480 | 1 | 1000 | IL-8 | sc-7922 | 2 | 800 |
| Endorphin beta | MAB0905 | 1 | 100 | IL-10 | sc-7888 | 2 | 800 |
| CARD 9 | 905-188 | 1 | 600 | iNOS | KAP-NO001 | 1 | 30 |
| Caspase 8 | AAP-118 | 1 | 50 | Jun | KAP-TF105 | 1 | 150 |
| Cyclin D1 | KAM-CC200 | 1 | 100 | Laminin | PU078-UP | 1 | 150 |
| Cox-2 | sc-7951 | 2 | 600 | Leptin receptor | sc-8391 | 2 | 10 |
| Cytochrome 450 | MFO-100 | 1 | 600 | Metallothionein | MO639 | 3 | 15 |
| CYP450 reductase | OSA-300 | 1 | 1000 | Mekk-1 | KAP-SA001E | 1 | 100 |
| EGFR | sc-03 | 2 | 150 | Mek-1 | KAP-MA010E | 1 | 400 |
| Ferritin | A0133 | 3 | 3000 | MMP-9 | 905-486 | 1 | 1500 |
| Fos | 905-640 | 1 | 10 | p53 | KAM-CC002 | 1 | 50 |
| Glucocorticoid receptor | sc-8992 | 2 | 600 | PBR | sc-20120 | 2 | 400 |
| GroEL | SPS-875 | 1 | 600 | Saliva alpha amylase | sc-25562 | 2 | 500 |
| Grp58 | SPA-580 | 1 | 1000 | Serotonin | sc-73024 | 2 | 10 |
| Grp75 | SPA-825 | 1 | 50 | Serotonin R1A | 905-741-100 | 1 | 100 |
| GSTp | A3600 | 3 | 1000 | Substance P | sc-58591 | 2 | 100 |
| HO-1 | SPA-895 | 1 | 4000 | SOD Cu | SOD-100 | 1 | 800 |
| HSF-1 | SPA-901 | 1 | 600 | SOD EC | SOD-106 | 1 | 400 |
| Hsp 25 | SPA-801 | 1 | 400 | SOD Mn | SOD-110 | 1 | 600 |
| Hsp 27 | SPA-800 | 1 | 100 | TGF beta | sc-7892 | 2 | 400 |
| Hsp 40 | SPA-400 | 1 | 150 | VIP | sc-20727 | 2 | 100 |
| Hsp 60 | SPA-804 | 1 | 750 | ALR | sc-33219 | 2 | 250 |
| Hsp 70 | SPA-810 | 1 | 1000 | AQP5 | sc-28628 | 2 | 600 |
| Hsp 90 | SPA-830 | 1 | 20 | BGT-1 | B1082-10 | 4 | 100 |
| IL-1 beta | sc-7884 | 2 | 800 | SAPK | KAP-SA011 | 1 | 50 |
| IL-6 | sc-7920 | 2 | 1000 | p38-MAPK | KAP-MA022 | 1 | 30 |

M, manufacturer: 1-Assay Designs, Ann Arbor, MI. 2-Santa Cruz Biotechnology, Santa Cruz, CA. 3-Dako, Carpinteria, CA. 4-US Biological, Swampscott, MA.
DF, dilution factor.

The ELISA assay. Methods in Examples 1 and 2 were used to prepare reference samples for the assay: protein lysates of the N and S pools. The tested biomarker was analyzed using a commercial ELISA assay using methods and the control ELISA assay as described in Example 1. The assay was optimized to achieve benchmark values for critical assay parameters as described in Example 1. For large marker panels, the development of a multiplexed ELISA assay (e.g. the 8-plex MultiBead ELISA, Assay Designs) was preferred over the single ELISA assay based on nearly 20-fold lower sample volume per analyte and lower cost per sample for the multiplexed ELISA.

Example 4

Determination of Baseline Concentrations for Salivary Biomarkers

This experiment provides an exemplary method for measuring baseline concentrations of saliva biomarkers using two complementary assays, ICC for cell-associated biomarkers in saliva smears, and ELISA for soluble biomarkers in saliva lysates. The method uses reference reagents and materials prepared in vitro as described in Example 2.

Saliva samples (3 ml) were collected from 10 healthy volunteers at 6 time points (3 days, 8 am and 3 pm) and used to prepare "individual smears" and "individual lysates" using methods from Example 1. On the first collection day, 1 ml aliquots of each sample were combined (20 ml) and used to prepare smears and protein lysates in N and S pools using Methods from Examples 1 and 2. Methods from Example 3 were used to validate saliva ICC and ELISA assays of the tested biomarker.

SI was determined for each smear using image analysis method from Example 1. The baseline was calculated as the average of the mean SI measurements in the individual samples. Individual and daily variability was determined as the standard deviation from the baseline.

Using the validated ELISA assay, the tested biomarker was measured in duplicate samples of individual lysates. Protein lysates of the N pool and S pool were and used as reference samples with normal and increased levels of saliva biomarkers. The baseline was calculated as the average concentration in the individual samples. Individual and daily variability was determined as the standard deviation from the baseline.

Example 5

Construction of a Biomarker Panel for Salivary Diagnostics

This experiment provides an exemplary method for constructing a biomarker panel that is useful for salivary diagnostics of health disorders.

Potential markers. Potential markers were identified using two methods: (1) Articles describing the molecular mechanism of cellular stress responses (SR) associated with health disorders were collected from peer-reviewed scientific literature. Meta-analysis of the articles was used to select potential biomarkers based on their association with one or more universal SR pathways that are activated in different cell types during more than one health disorder[4-7]. Ten universal SR pathways are described in Table 1. (2) Protein lysates of the N pool and S pool were prepared using methods from Example 2. The lysates were analyzed to identify differentially expressed proteins and peptides using a method with a sufficiently high sensitivity and peptide separation to enable reliable sequencing and identification of peptides in a complex protein mixture such as the saliva lysate, for example the isotopic labeling coupled with liquid chromatography tandem mass spectrometry (IL-LC-MS/MS). Potential biomarkers were identified based on more than 2-fold difference in the concentration between the S and N pools.

Candidate marker panel. Reference slides and protein lysates were prepared from the N pool, S pool and treated cultures T1-T5 using methods from Examples 1 and 2. Methods from Example 3 were used to validate ICC and ELISA immunoassays for potential saliva markers. Methods from Example 4 were used to measure the normal baseline and variability of the potential markers. Candidate biomarkers were selected from the potential biomarkers using following criteria: (1) Each marker had a stable baseline in normal saliva based on less than 2-fold individual and daily differences in the marker concentration. In such markers, the ratio between the baseline concentration and the standard deviation of the baseline is less than 0.65. (2) The concentration of each marker was more than 3-fold different between the S and N pools. Preferred markers had more than 3-fold increased concentration in the S pool relative to the N pool. (3) When combined into a panel, the markers discriminated between the T1-T5 saliva samples. A panel of 52 candidate salivary biomarkers identified using this method is shown in Table 5 and FIGS. 2-5.

Initial clinical validation. A small-scale clinical study was used to demonstrate that a candidate marker panel had a potential diagnostic value for a specific medical condition. Clinical saliva samples and gold standard indicators of the medical condition were collected using methods from Example 1. A practical limit for the volume of clinical saliva samples was about 3 ml since in many medical conditions patients cannot produce as much saliva as healthy people. The saliva samples were processed into saliva smears and protein lysates using methods from Example 1. Individual biomarkers were measured in the smears and lysates using the validated ICC and ELISA assays. The assays used reference slides and lysates with normal and increased levels of saliva biomarkers (the N pool and S pool) prepared from normal saliva using methods from Examples 1 and 2. The discrimination of the medical condition using the saliva biomarker panel was determined using correlation analysis with the gold standard indicator. The diagnostic accuracy of the saliva biomarker for the threshold value of the gold standard indicator was determined using the Receiver Operator Characteristics (ROC) curve analysis, which provided the criterion values (cutoff sensitivity and specificity values that divide true negatives and true positives) and the Area-Under-Curve value (AUC)[13-15]. Optimized biomarker panel was constructed by combining a minimal number of markers that classified the medical condition with the greatest AUC value and the most narrow range of criterion values.

Large-scale clinical validation. To efficiently measure biomarkers in large sample sets, a multiplexed ELISA assay for the optimized saliva biomarker panel was produced using a commercial assay platform such in such as MultiBead ELISA (Assay Designs) and methods from Example 3. The assay used reference lysates with normal and increased levels of saliva biomarkers (the N pool and S pool) prepared from normal saliva using methods from Examples 1 and 2. Biomarker measurements obtained by the multiplexed ELISA were used to construct the final biomarker panel that accurately discriminated the specific medical condition and was not affected by potentially confounding variables such as gender, age and other medical conditions.

The final biomarker panel was used for the forward design of a commercial diagnostic test using a mature assay technology with proven acceptability by regulators and customers such as the lateral-flow immunoassay (LFIA)[16-17]. The multiplexed ELISA assay was used as the reference assay in the testing of the commercial test. The prototype test was optimized using reference lysates with normal and increased levels of saliva biomarkers (the N pool and S pool) prepared from normal saliva using methods from Examples 1 and 2.

Example 6

Saliva Test for Monitoring Hydration Status

A rapid saliva test for ≥3% dehydration has been developed using following steps: (1) A candidate panel of 52 SR markers (see Table 5) was constructed using methods from Example 5. (2) The initial clinical validation of the panel used methods from Example 5 and a laboratory study of dehydration induced in healthy volunteers (n=15) by exercise in heat without fluid intake. The study design discriminated between effects of dehydration and exercise-heat. Stable euhydration before the trial was documented based on consistent body mass (±1%), plasma osmolality <290 mOsmol/kg, urine specific gravity <1.02 for 3 days[56]. During the trial, progressive dehydration from 1 to 6% was monitored by 1-4% weight loss. Samples of saliva, blood and urine were collected at 9 time points. The blood and urine samples were used for standard laboratory tests of the hydration status including the gold standard test (plasma osmolality). The clinical saliva samples were collected and processed into smears and protein lysates using methods from Example 1. Individual 52 SR markers were measured in the smears and lysates using optimized ICC and ELISA protocols as described in Example 5. The assays used reference slides and lysates with normal and increased levels of saliva biomarkers (the N pool and S pool) prepared from normal saliva using methods from Examples 1 and 2. The SR marker measurements were correlated with plasma osmolality to determine whether the SR marker measurements were significantly related to plasma osmolality and not affected by potentially confounding effects of exercise-heat, gender and sampling variables. The diagnostic accuracy of the SR markers for the plasma osmolality threshold (296 mOsmol/kg indicating 3% dehydration) was determined using the ROC curve analysis as described in Example 5. A minimal panel of SR markers that had the best diagnostic accuracy for ≥3% dehydration was selected using methods from Example 5.

(3) Methods from Example 5 and a large clinical study of dehydration (n=100) were used to construct the optimized SR marker panel. (4) The optimized SR marker panel was used to produce a prototype LFIA device. The prototype was optimized using reference saliva lysates as described in Example 5. The optimized prototype was tested extensively using clinical saliva samples to demonstrate reliability, accuracy, applicability for field use and regulatory requirements. The multiplexed ELISA assay was used as a reference assay for the LFIA. The LFIA device showed actionable levels of dehydration based on plasma osmolality thresholds: normal (plasma osmolality ≤290 mOsmol/kg), moderately dehydrated (2-3% dehydration, osmolality 291-296) and severely dehydrated (dehydration >3%, osmolality >296), see FIG. 6. The benefit of identifying moderate dehydration is that it can be treated in the field by simple oral rehydration that prevents progression to severe dehydration that might require hospitalization and intravenous rehydration.

Example 7

Saliva Test for Monitoring HIV/AIDS Risk and Treatment Outcome

A rapid saliva test for predicting AIDS risk treatment outcome has been developed using following steps: (1) A candidate panel of 52 SR markers (Table 5) was constructed using methods from Example 5. (2) The initial clinical validation of the panel used methods from Example 5 and saliva samples from HIV/AIDS patients (n=100) with CD4 counts >500, 200-500 and <200 cells/mm$^3$. The study subjects had stable CD4 counts during 6 months before enrollment, and also at when tested during the office visit when the saliva sample was collected[68,70-71]. The clinical saliva samples were collected and processed into smears and protein lysates using methods from Example 1. The individual 52 SR markers were measured in the smears and lysates using optimized ICC and ELISA protocols as described in Example 5. The assays used reference slides and lysates with normal and increased levels of saliva biomarkers (the N pool and S pool) prepared from normal saliva using methods from Examples 1 and 2. SR marker measurements in the clinical saliva samples were correlated with matched CD4 counts (the CD4 count measured during the same office visit when the saliva was collected). The diagnostic accuracy of the SR markers for threshold CD4 counts (≥500 and ≤200 cells/mm$^3$) was determined using the ROC curve analysis as described in Example 5. A minimal panel of SR markers with the best diagnostic accuracy for the threshold CD4 counts was selected using methods from Example 5.

(3) Saliva samples were collected from HIV patients (n=100) at 5 time points during the initial year of the first-line cART. Prior the enrollment, patients had suppressed baseline viral load of ≥500 copies/ml and a baseline CD4 count <200 cells/mm$^3$. Benchmarks for successful cART outcome after 9 months (expected in 70-90% of the patients) were: viral load <50 copies/ml, CD4 count increased ≥100 cells/mm3 above the baseline and no AIDS-defining event or death[68-73]. The minimal panel of SR markers produced by the previous study was measured in saliva lysates using multiplexed ELISA as described in Example 5. SR marker measurements were correlated with CD4 count and viral load to determine the prognostic accuracy of SRP markers for cART outcome. The benchmark for prognostic accuracy was the hazard ratio from Cox proportional hazards models at 95% confidence interval. The benchmark for prognostic independence were higher critical chi-square values for Cox models containing SR markers compared to models with CD4 count and viral load alone[69,72]. Results of the study were used to optimize the minimal SR marker panel as outlined in Example 5.

(4) The optimized minimal SR marker panel was used to produce a prototype LFIA device. The prototype was optimized using reference saliva lysates as described in Example 5. The optimized prototype was tested extensively using clinical saliva samples to demonstrate reliability, accuracy, applicability for field use and regulatory requirements. The multiplexed ELISA assay was used as a reference assay for the LFIA. The LFIA device showed actionable levels of AIDS risk based on threshold CD4 counts: low (CD4 count >500 cells/mm$^3$), moderate (CD4 count 500-200 cells//mm$^3$) or high (CD4 count <200 cells). The benefit of identifying a moderate AIDS risk is that it indicates the need for starting or modifying cART therapy to prevent progression to severe AIDS risk.

Example 8

SRP Analysis of Post-Traumatic Psychological Stress

Multi-SRP assay of saliva was applied to the study of post-traumatic psychological stress. Multi-SRP scores were measured in salivary cells (FIG. 8a). The scores strongly correlated with self-reported health status and provided actionable health care information: normal daily activities were possible at baseline and mildly elevated multi-SRP scores, and bed rest was needed at high multi-SRP scores (FIG. 8b).

FIG. 7: Multi-SRP scores during post-traumatic psychological distress. Saliva samples were collected from a healthy subject at different time points before and after psychological trauma. a, Multi-SRP staining of saliva cells. Original magnifications: ×200. b, The SRP score was calculated as the ratio between the average staining intensity across 900 saliva cells, and the maximum staining intensity value for saliva cells. The staining intensity was quantified using image analysis. Baseline was calculated as the average across multi-SRP scores for six time points before the psychological stress. The error bars are standard deviations. During the psychological distress, multi-SRP scores correlated with the functional state. Normal daily activities were possible till Day 8 when fatigue was reported. Health status deteriorated on Day 12 and a bedrest was required due to dizziness and nausea. Normal health status was reported on Day 45 post trauma.

Although the invention has been described with reference to the above examples, it will be understood that modifications and variations are encompassed within the spirit and scope of the invention. Accordingly, the invention is limited only by the following claims.

1. Chiappin, S., Antonelli, G., Gatti, R. & De Palo, E. F. Saliva specimen: a new laboratory tool for diagnostic and basic investigation. Clin Chim Acta 383, 30-40 (2007).
2. Nishanian, P., Aziz, N., Chung, J., Detels, R. & Fahey, J. L. Oral fluids as an alternative to serum for measurement of markers of immune activation. Clin Diagn Lab Immunol 5, 507-12 (1998).
3. Streckfus, C. F. & Bigler, L. R. Saliva as a diagnostic fluid. Oral Dis 8, 69-76 (2002).
4. Southern, S. O. U.S. Provisional Patent Application "Devices and Methods for Early Detection of Chronic Stress and Health Disorders." Application Ser. No. 60/910,158. Filing Date Apr. 4, 2007. (2007).
5. Southern, S. O. International Patent Application entitled "Systems and Methods for Analyzing Persistent Homeostatic Perturbations." Application Serial No. PCT/US2008/004448. Filing Date Apr. 4, 2008. Claiming priority to U.S. Patent Application Ser. No. 60/910,158 filed Apr. 4, 2007. (2008).
6. Southern, S. O. U.S. National Stage Patent Application entitled "Systems and Methods for Analyzing Persistent Homeostatic Perturbations". Serial No. PCT/US2008/004448. Filing Date Sep. 12, 2008. Claiming priority to U.S. Patent Application Ser. No. 60/910,158 filed Apr. 4, 2007. (2008).
7. Southern, S. O. U.S. Provisional Patent Application entitled "Health Test for a Broad Spectrum of Health Problems". Application Ser. No. 61/102,341. Filing Date Oct. 2, 2008. (2008).

8. Rhodus, N. L. et al. A comparison of the pro-inflammatory, NF-kappaB-dependent cytokines: TNF-alpha, IL-1-alpha, IL-6, and IL-8 in different oral fluids from oral lichen planus patients. Clin Immunol 114, 278-83 (2005).
9. Streckfus, C., Mayorga-Wark, O, Daniel Arreola, D, Edwards, C, Bigler, L, Dubinsky, W P. A Comparison of the Oncoproteomic Profiles in Pooled Saliva Specimens from Individuals Diagnosed With Stage IIa and Stage IIb Ductal Carcinoma of the Breast and Healthy Controls. Breast Cancer Res in Review (2009).
10. Tan, W. et al. Optical protein sensor for detecting cancer markers in saliva. Biosens Bioelectron 24, 266-71 (2008).
11. Huang, Z. & Tunnacliffe, A. Response of human cells to desiccation: comparison with hyperosmotic stress response. J Physiol 558, 181-91 (2004).
12. Hang, H., He, L. & Fox, M. H. Cell cycle variation of Hsp70 levels in HeLa cells at 37 degrees C. and after a heat shock. J Cell Physiol 165, 367-75 (1995).
13. Bossuyt, P. M. et al. Towards complete and accurate reporting of studies of diagnostic accuracy: the STARD initiative. Fam Pract 21, 4-10 (2004).
14. de Vries, S. O., Hunink, M. G. & Polak, J. F. Summary receiver operating characteristic curves as a technique for meta-analysis of the diagnostic performance of duplex ultrasonography in peripheral arterial disease. Acad Radiol 3, 361-9 (1996).
15. Singh, G. Determination of Cutoff Score for a Diagnostic Test. The Internet Journal of Laboratory Medicine 2 (2007).
16. O'Farrell, B. Developing approaches to the development and manufacture of highly sensitive, reproducible lateral flow assays. Proceedings of the Oak Ridge National Conference. (2006).
17. Park, R. Lateral-flow POC tests to grow. Medical Device Link. May (2007).
18. Institute of Medicine. Hydration status monitoring. In: Monitoring Metabolic Status: Predicting Decrements in Physiological and Cognitive Performance. Washington, D.C.: National Academy Press, 2004, pp. 270-280. (2004).
19. Casa, D. J., Clarkson, P. M. & Roberts, W. O. American College of Sports Medicine roundtable on hydration and physical activity: consensus statements. Curr Sports Med Rep 4, 115-27 (2005).
20. Montain, S. J., Cheuvront, S. N., Carter, R. III, Sawka, M. N. Human water and electrolyte balance. In: Present Knowledge in Nutrition. B. A. Bowman and R. M. Russell Eds., Washington, D.C., ILSI Life Sciences, pp. 422-429. (2006).
21. Sawka, M. N., Cheuvront, S. N. & Carter, R., 3rd. Human water needs. Nutr Rev 63, S30-9 (2005).
22. World Health Organization. The treatment of diarrhea: A manual for physicians and other senior health workers. Geneva, Switzerland. (1995).
23. American Dietetic Association. Position of the American Dietetic Association: Oral Health and Nutrition Journal of the American Dietetic Association, 107 (8), p. August 2007 107, 1418-1428 (2007).
24. Joint Human Performance Enhancement (JHPE) capability vision. USAMRMC S&T Planning Workshop. Mar. 7, 2008 (2008).
25. Boersma, F., Van Den Brink, W., Deeg, D. J., Eefsting, J. A. & Van Tilburg, W. Survival in a population-based cohort of dementia patients: predictors and causes of mortality. Int J Geriatr Psychiatry 14, 748-53 (1999).
26. Carter, R., 3rd, Cheuvront, S. N. & Williams, J. O. Epidemiology of hospitalizations and deaths from heat illness in soldiers. Med Sci Sports Exerc 37, 1338-44 (2005).
27. Chassagne, P., Druesne, L., Capet, C., Menard, J. F. & Bercoff, E. Clinical presentation of hypernatremia in elderly patients: a case control study. J Am Geriatr Soc 54, 1225-30 (2006).
28. Cheuvront, S. N., Sawka, M. N. Hydration assessment of athletes. Sports Science Exchange 18, 1-6 (2005).
29. Cheuvront, S. N., Carter, R., 3rd & Sawka, M. N. Fluid balance and endurance exercise performance. Curr Sports Med Rep 2, 202-8 (2003).
30. Cheuvront, S. N., Montain, S. J. & Sawka, M. N. Fluid replacement and performance during the marathon. Sports Med 37, 353-7 (2007).
31. Chuang, S.-F., Sung, J.-M., Kuo, S.-C., Huang, J.-J., Lee, S.-Y. Oral and dental manifestations in diabetic and non-diabetic uremic patients receiving hemodialysis Oral Surgery, Oral Medicine, Oral Pathology, Oral Radiology & Endodontology 99, 689-695 (2005).
32. Conno, F. D., Ripamonti, C., Sbanotto, A., Ventafridda, V. Oral complications in patients with advanced cancer Journal of Pain and Symptom Management 4, 20-30 (1989).
33. Dalal, S., Bruera, E. Dehydration in cancer patients: to treat or not to treat. The Journal of Supportive Oncology 2, 467-479 (2004).
34. Diggins, K. C. Treatment of mild to moderate dehydration in children with oral rehydration therapy. J Am Acad Nurse Pract 20, 402-6 (2008).
35. Emond, S. Evidence-based emergency medicine/rational clinical examination abstract. Dehydration in infants and young children. Ann Emerg Med 53, 395-7 (2009).
36. Goldman, R. D., Friedman, J. N. & Parkin, P. C. Validation of the clinical dehydration scale for children with acute gastroenteritis. Pediatrics 122, 545-9 (2008).
37. Kooman, J. P., van der Sande, F. M. & Leunissen, K. M. Wet or dry in dialysis—can new technologies help? Semin Dial 22, 9-12 (2009).
38. Lieberman, H. R. et al. Severe decrements in cognition function and mood induced by sleep loss, heat, dehydration, and undernutrition during simulated combat. Biol Psychiatry 57, 422-9 (2005).
39. Macy, M. e. a. Trends in High-Turnover Stays Among Children Hospitalized in the United States, 1993-2003. PEDIATRICS 123, 996-1002 (2009).
40. McConnochie, K. M., Conners, G. P., Lu, E. & Wilson, C. How commonly are children hospitalized for dehydration eligible for care in alternative settings? Arch Pediatr Adolesc Med 153, 1233-41 (1999).
41. Merenstein, D., Egleston, B. & Diener-West, M. Lengths of stay and costs associated with children's hospitals. Pediatrics 115, 839-44 (2005).
42. Paul, I. M., Phillips, T. A., Widome, M. D. & Hollenbeak, C. S. Cost-effectiveness of postnatal home nursing visits for prevention of hospital care for jaundice and dehydration. Pediatrics 114, 1015-22 (2004).
43. Rypkema, G. et al. Cost-effectiveness of an interdisciplinary intervention in geriatric inpatients to prevent malnutrition. J Nutr Health Aging 8, 122-7 (2004).
44. Sawka M N, B. L., Eichner E R, Maughan R J, Montain S J, and Stachenfeld N S. American College of Sports Medicine Position Stand. Exercise and Fluid Replacement. Med. Sci Sports Exerc 39 337-90 (2007).
45. Scully, C. F., D. H. Oral Medicine—Update for the dental practitioner: Dry mouth and disorders of salivation British Dental Journal 199, 423-427 (2005).
46. Smith, S. Clinical signs of dehydration in children. Emerg Med J 24, 605 (2007).

47. Thomas, D. R., Tariq, S. H., Makhdomm, S., Haddad, R. & Moinuddin, A. Physician misdiagnosis of dehydration in older adults. J Am Med Dir Assoc 4, 251-4 (2003).
48. Van der Riet, P., Brooks, D., Ashby, M. Nutrition and hydration at the end of life. J Law Med 14, 182-98 (2006).
49. Wakefield, B., Mentes, J., Diggelmann, L. & Culp, K. Monitoring hydration status in elderly veterans. West J Nurs Res 24, 132-42 (2002).
50. Wakefield, B. J., Mentes, J., Holman, J. E. & Culp, K. Risk factors and outcomes associated with hospital admission for dehydration. Rehabil Nurs 33, 233-41 (2008).
51. Warren, J. L. et al. The burden and outcomes associated with dehydration among US elderly, 1991. Am J Public Health 84, 1265-9 (1994).
52. Xiao, H., Barber, J. & Campbell, E. S. Economic burden of dehydration among hospitalized elderly patients. Am J Health Syst Pharm 61, 2534-40 (2004).
53. Almond, C. Hyponatremia among runners in the Boston Marathon The New England Journal Of Medicine 352, 1550-6 (2005).
54. Florida initiative aims to slash unnecessary admissions due to 'catch-all' dehydration diagnosis. Clin Resour Manag 2, 77-9, 65 (2001).
55. Dimant, J. Delivery of nutrition and hydration care in nursing homes: assessment and interventions to prevent and treat dehydration, malnutrition, and weight loss. J Am Med Dir Assoc 2, 175-82 (2001).
56. Popowski, L. A. et al. Blood and urinary measures of hydration status during progressive acute dehydration. Med Sci Sports Exerc 33, 747-53 (2001).
57. Shirreffs, S. M., Taylor, A. J., Leiper, J. B. & Maughan, R. J. Post-exercise rehydration in man: effects of volume consumed and drink sodium content. Med Sci Sports Exerc 28, 1260-71 (1996).
58. Montain, S. J., Ely, M. R. & Cheuvront, S. N. Marathon performance in thermally stressing conditions. Sports Med 37, 320-3 (2007).
59. US Army Medical Research and Materiel Command Task Area T: Warfighter Protection and Injury Preventionin Extreme Environments, Environmental Health and Protection Program Area (new task effective FY09 replacing Technology Objective (ATO) Biomedical Enablers of Operational Health and Performance (IV.MD.2006-01). (2008).
60. McGown, C. M. et al. Gold medal volleyball: the training program and physiological profile of the 1984 Olympic champions. Res Q Exerc Sport 61, 196-200 (1990).
61. O'Brien, K. K. et al. Hyponatremia associated with overhydration in U.S. Army trainees. Mil Med 166, 405-10 (2001).
62. Godek, S. F., Bartolozzi, A. R., Burkholder, R., Sugarman, E. & Dorshimer, G. Core temperature and percentage of dehydration in professional football linemen and backs during preseason practices. J Athl Train 41, 8-14; discussion 14-7 (2006).
63. Oppliger, R. A. & Bartok, C. Hydration testing of athletes. Sports Med 32, 959-71 (2002).
64. Albert, S. G., Nakra, B. R., Grossberg, G. T. & Caminal, E. R. Drinking behavior and vasopressin responses to hyperosmolality in Alzheimer's disease. Int Psychogeriatr 6, 79-86 (1994).
65. Montain, S. J. C., S N; Sawka, M N Exercise associated hyponatraemia: quantitative analysis to understand the aetiology. British Journal of Sports Medicine 41, 98-105 (2006).
66. Chumlea, W. C. et al. Total body water reference values and prediction equations for adults. Kidney Int 59, 2250-8 (2001).
67. Campsmith, M., Rhodes, P, Hall, H I, Green, T. HIV prevalence estimates—United States, 2006 MMWR, Centers for Disease Control and Prevention 57, 1073-1076 (2008).
68. Department of Health and Human Services. Guidelines for the use of antiretroviral agents in HIV-1-infected adults and adolescents. http://aidsinfo.nih.gov/ContentFiles/AdultandAdolescentGL.pdf. (2008).
69. Langford, S. E., Ananworanich, J. & Cooper, D. A. Predictors of disease progression in HIV infection: a review. AIDS Res Ther 4, 11 (2007).
70. Khanlou, H., Guyer, B. & Farthing, C. Efficacy of tenofovir as intensification of zidovudine/lamivudine/abacavir fixed-dose combination in the treatment of HIV-positive patients. J Acquir Immune Defic Syndr 38, 627-8 (2005).
71. Ortiz, R. et al. Efficacy and safety of once-daily darunavir/ritonavir versus lopinavir/ritonavir in treatment-naive HIV-1-infected patients at week 48. Aids 22, 1389-97 (2008).
72. Kulkarni, H. et al. CCL3L1-CCR5 genotype improves the assessment of AIDS Risk in HIV-1-infected individuals. PLoS ONE 3, e3165 (2008).
73. Mitsuyasu, R. T. et al. Phase 2 gene therapy trial of an anti-HIV ribozyme in autologous CD34+ cells. Nat Med 15, 285-92 (2009).
74. Liu, F. R. et al. Correlation analysis on total lymphocyte count and CD4 count of HIV-infected patients. Int J Clin Pract 62, 955-60 (2008).

What is claimed is:

1. A method for detecting a condition or disorder associated with a stress response in a subject, comprising:
(i) obtaining from the subject a biological sample comprising an adequate whole cell count comprising whole salivary cells, wherein the cells contain biomarkers;
(ii) determining that a control sample contains an adequate whole cell count; and
(iii) measuring levels of stress response (SR) biomarkers in a panel, wherein detection of an altered level of at least one SR biomarker in the biological sample, as compared to the control sample is indicative of a condition or disorder associated with a stress response, thereby detecting the condition or disorder in the subject.

2. The method of claim 1, wherein the at least one stress response biomarker is selected from the group consisting of aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide.

3. The method of claim 2, wherein the at least one stress biomarker is associated with dehydration.

4. The method of claim 2, wherein the at least one stress biomarker is associated with AIDS progression.

5. The method of claim 2, wherein the levels of the at least one biomarker are detected by analysis of biomarker protein or nucleic acid in the sample comprising the salivary cells.

6. The method of claim 5, wherein the analysis of biomarker protein includes detection with an antibody.

7. The method of claim 6, wherein the salivary cells are lysed prior to analysis with the antibody.

8. The method of claim 6, wherein the analysis is by ELISA.

9. The method of claim 1, wherein the sample comprising the salivary cells is analyzed on microscope slide.

10. The method of claim 5, wherein the analysis of biomarker nucleic acid comprises isolation of salivary cell nucleic acid.

11. The method of claim 10, wherein the biomarker nucleic acid is detected in the isolated salivary cell nucleic acid by nucleic acid hybridization or PCR amplification.

12. The method of claim 1, wherein the levels of the biomarkers are detected using a device, comprising:
(a) a disposable module for uptake of a test sample and reagent storage, wherein the module comprises reagents for assaying for at least one stress response biomarker; and
(b) a reusable module for signal detection and result display; wherein the reusable module displays a signal that indicates the presence of the at least one stress response biomarker in the test sample, thereby detecting the condition or disorder in the subject.

13. The method of claim 1, wherein the condition or disorder is dehydration or traumatic brain injury (TBI).

14. The method of claim 1, wherein the salivary cells are collected using an oral brush.

15. The method of claim 1, wherein the control sample comprises at least one of epithelial cells or leukocytes.

16. The method of claim 1, wherein the control sample comprises viable cells.

17. The method of claim 1, wherein the adequate cell count is approximately $5 \times 10^5$ cells/ml or greater.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
atgaccaaca agtgtctcct ccaaa                25

<210> SEQ ID NO 2
<211> LENGTH: 25
<212> TYPE: DNA

```
<213> ORGANISM: Artificial Sequence
<220> FEATURE:
<223> OTHER INFORMATION: Primer

<400> SEQUENCE: 2
gtttcggagg taacctgtaa gtctg                                          25
```